(12) United States Patent
Burd et al.

(10) Patent No.: US 9,696,309 B2
(45) Date of Patent: Jul. 4, 2017

(54) METHODS OF MEASURING LEVELS OF PHOSPHORYLATED NEURONAL NITRIC OXIDE SYNTHASE

(71) Applicants: THE JOHNS HOPKINS UNIVERSITY, Baltimore, MD (US); KENNEDY KRIEGER INSTITUTE, INC., Baltimore, MD (US)

(72) Inventors: Irina Burd, Silver Spring, MD (US); Talaibek Borbiev, Rockville, MD (US); Elisabeth Nigrini, Baltimore, MD (US); Michael Johnston, Baltimore, MD (US)

(73) Assignees: The Johns Hopkins University, Baltimore, MD (US); Kennedy Krieger Institute, Inc., Baltimore, MD (US)

( * ) Notice: Subject to any disclaimer, the term of this patent is extended or adjusted under 35 U.S.C. 154(b) by 213 days.

(21) Appl. No.: 14/408,393

(22) PCT Filed: Dec. 7, 2012

(86) PCT No.: PCT/US2012/068425
§ 371 (c)(1),
(2) Date: Dec. 16, 2014

(87) PCT Pub. No.: WO2013/086306
PCT Pub. Date: Jun. 13, 2013

(65) Prior Publication Data
US 2015/0247854 A1    Sep. 3, 2015

Related U.S. Application Data

(60) Provisional application No. 61/567,882, filed on Dec. 7, 2011, provisional application No. 61/668,654, filed on Jul. 6, 2012.

(51) Int. Cl.
*G01N 33/535* (2006.01)
*G01N 33/573* (2006.01)
*G01N 33/68* (2006.01)

(52) U.S. Cl.
CPC ......... *G01N 33/573* (2013.01); *G01N 33/535* (2013.01); *G01N 33/6896* (2013.01); *G01N 2333/90254* (2013.01); *G01N 2440/14* (2013.01); *G01N 2800/28* (2013.01)

(58) Field of Classification Search
None
See application file for complete search history.

(56) References Cited

PUBLICATIONS

Osuka, K., et al., "Phosphorylation of neuronal nitric oxide synthase at ser847 by CaM-KII in the hippocampus of rat brain after transient forebrain ischemia", J Cereb Blood Flow Metab (2002) vol. 22, No. 9, pp. 1098-1106.
Yan, X., et al., "Brain ischemia induces serine phosphorylation of neuronal nitric oxide synthase by Ca2+/calmodulin-dependent protein kinase II in rat hippocampus", Acta Pharmacol Sin, (2004) vol. 25, No. 5, pp. 617-622.
Rameau, G., et al., "Bidirectional regulation of neuronal nitric-oxide synthase phosphorylation at serine 847 by the N-methyl-D-aspartate receptor", The Journal of Biological Chemistry, (2004) vol. 279, No. 14, pp. 14307-14314.
Hayashi, Y., et al., "Regulation of neuronal nitric-oxide synthase by calmodulin kinases" The Journal of Biological Chemistry (1999) vol. 274, No. 29, pp. 20597-10602.

*Primary Examiner* — Robert C Hayes
(74) *Attorney, Agent, or Firm* — Johns Hopkins Technology Ventures

(57) ABSTRACT

The present invention relates to the field of biomarkers. More specifically, the present invention relates to biomarkers useful in diagnosing brain injuries. In a specific embodiment, a method for diagnosing perinatal brain injury in a patient comprises the steps of (a) determining the ratio of phosphorylated nNOS to unphosphorylated nNOS in a sample collected from the patient using an ELISA; and (b) comparing the ratio with predefined ratios of the same proteins that correlate to a patient having perinatal brain injury and predefined ratios of the same proteins that correlate to a patient not having perinatal brain injury, wherein a correlation to one of the predefined ratios provides the diagnosis.

2 Claims, 10 Drawing Sheets

SEQUENCE LISTING

```
<160> NUMBER OF SEQ ID NOS: 2

<210> SEQ ID NO 1
<211> LENGTH: 1434
<212> TYPE: PRT
<213> ORGANISM: Homo sapiens

<400> SEQUENCE: 1

Met Glu Asp His Met Phe Gly Val Gln Gln Ile Gln Pro Asn Val Ile
1               5                   10                  15

Ser Val Arg Leu Phe Lys Arg Lys Val Gly Gly Leu Gly Phe Leu Val
            20                  25                  30

Lys Glu Arg Val Ser Lys Pro Pro Val Ile Ile Ser Asp Leu Ile Arg
        35                  40                  45

Gly Gly Ala Ala Glu Gln Ser Gly Leu Ile Gln Ala Gly Asp Ile Ile
    50                  55                  60

Leu Ala Val Asn Gly Arg Pro Leu Val Asp Leu Ser Tyr Asp Ser Ala
65                  70                  75                  80

Leu Glu Val Leu Arg Gly Ile Ala Ser Glu Thr His Val Val Leu Ile
            85                  90                  95

Leu Arg Gly Pro Glu Gly Phe Thr Thr His Leu Glu Thr Thr Phe Thr
        100                 105                 110
```

-continued

Gly Asp Gly Thr Pro Lys Thr Ile Arg Val Thr Gln Pro Leu Gly Pro
            115                 120                 125

Pro Thr Lys Ala Val Asp Leu Ser His Gln Pro Pro Ala Gly Lys Glu
130                 135                 140

Gln Pro Leu Ala Val Asp Gly Ala Ser Gly Pro Gly Asn Gly Pro Gln
145                 150                 155                 160

His Ala Tyr Asp Asp Gly Gln Glu Ala Gly Ser Leu Pro His Ala Asn
                165                 170                 175

Gly Leu Ala Pro Arg Pro Pro Gly Gln Asp Pro Ala Lys Lys Ala Thr
            180                 185                 190

Arg Val Ser Leu Gln Gly Arg Gly Glu Asn Asn Glu Leu Leu Lys Glu
        195                 200                 205

Ile Glu Pro Val Leu Ser Leu Leu Thr Ser Gly Ser Arg Gly Val Lys
    210                 215                 220

Gly Gly Ala Pro Ala Lys Ala Glu Met Lys Asp Met Gly Ile Gln Val
225                 230                 235                 240

Asp Arg Asp Leu Asp Gly Lys Ser His Lys Pro Leu Pro Leu Gly Val
                245                 250                 255

Glu Asn Asp Arg Val Phe Asn Asp Leu Trp Gly Lys Gly Asn Val Pro
            260                 265                 270

Val Val Leu Asn Asn Pro Tyr Ser Glu Lys Glu Gln Pro Pro Thr Ser
        275                 280                 285

Gly Lys Gln Ser Pro Thr Lys Asn Gly Ser Pro Ser Lys Cys Pro Arg
    290                 295                 300

Phe Leu Lys Val Lys Asn Trp Glu Thr Glu Val Val Leu Thr Asp Thr
305                 310                 315                 320

Leu His Leu Lys Ser Thr Leu Glu Thr Gly Cys Thr Glu Tyr Ile Cys
                325                 330                 335

Met Gly Ser Ile Met His Pro Ser Gln His Ala Arg Arg Pro Glu Asp
            340                 345                 350

Val Arg Thr Lys Gly Gln Leu Phe Pro Leu Ala Lys Glu Phe Ile Asp
        355                 360                 365

Gln Tyr Tyr Ser Ser Ile Lys Arg Phe Gly Ser Lys Ala His Met Glu
    370                 375                 380

Arg Leu Glu Glu Val Asn Lys Glu Ile Asp Thr Thr Ser Thr Tyr Gln
385                 390                 395                 400

Leu Lys Asp Thr Glu Leu Ile Tyr Gly Ala Lys His Ala Trp Arg Asn
                405                 410                 415

Ala Ser Arg Cys Val Gly Arg Ile Gln Trp Ser Lys Leu Gln Val Phe
            420                 425                 430

Asp Ala Arg Asp Cys Thr Thr Ala His Gly Met Phe Asn Tyr Ile Cys
        435                 440                 445

Asn His Val Lys Tyr Ala Thr Asn Lys Gly Asn Leu Arg Ser Ala Ile
    450                 455                 460

Thr Ile Phe Pro Gln Arg Thr Asp Gly Lys His Asp Phe Arg Val Trp
465                 470                 475                 480

Asn Ser Gln Leu Ile Arg Tyr Ala Gly Tyr Lys Gln Pro Asp Gly Ser
                485                 490                 495

Thr Leu Gly Asp Pro Ala Asn Val Gln Phe Thr Glu Ile Cys Ile Gln
            500                 505                 510

Gln Gly Trp Lys Pro Pro Arg Gly Arg Phe Asp Val Leu Pro Leu Leu
        515                 520                 525

Leu Gln Ala Asn Gly Asn Asp Pro Glu Leu Phe Gln Ile Pro Pro Glu

```
                     530                 535                 540
Leu Val Leu Glu Val Pro Ile Arg His Pro Lys Phe Glu Trp Phe Lys
545                 550                 555                 560

Asp Leu Gly Leu Lys Trp Tyr Gly Leu Pro Ala Val Ser Asn Met Leu
                565                 570                 575

Leu Glu Ile Gly Gly Leu Glu Phe Ser Ala Cys Pro Phe Ser Gly Trp
            580                 585                 590

Tyr Met Gly Thr Glu Ile Gly Val Arg Asp Tyr Cys Asp Asn Ser Arg
            595                 600                 605

Tyr Asn Ile Leu Glu Glu Val Ala Lys Lys Met Asn Leu Asp Met Arg
        610                 615                 620

Lys Thr Ser Ser Leu Trp Lys Asp Gln Ala Leu Val Glu Ile Asn Ile
625                 630                 635                 640

Ala Val Leu Tyr Ser Phe Gln Ser Asp Lys Val Thr Ile Val Asp His
                645                 650                 655

His Ser Ala Thr Glu Ser Phe Ile Lys His Met Glu Asn Glu Tyr Arg
            660                 665                 670

Cys Arg Gly Gly Cys Pro Ala Asp Trp Val Trp Ile Val Pro Pro Met
            675                 680                 685

Ser Gly Ser Ile Thr Pro Val Phe His Gln Glu Met Leu Asn Tyr Arg
        690                 695                 700

Leu Thr Pro Ser Phe Glu Tyr Gln Pro Asp Pro Trp Asn Thr His Val
705                 710                 715                 720

Trp Lys Gly Thr Asn Gly Thr Pro Thr Lys Arg Arg Ala Ile Gly Phe
                725                 730                 735

Lys Lys Leu Ala Glu Ala Val Lys Phe Ser Ala Lys Leu Met Gly Gln
            740                 745                 750

Ala Met Ala Lys Arg Val Lys Ala Thr Ile Leu Tyr Ala Thr Glu Thr
            755                 760                 765

Gly Lys Ser Gln Ala Tyr Ala Lys Thr Leu Cys Glu Ile Phe Lys His
        770                 775                 780

Ala Phe Asp Ala Lys Val Met Ser Met Glu Glu Tyr Asp Ile Val His
785                 790                 795                 800

Leu Glu His Glu Thr Leu Val Leu Val Val Thr Ser Thr Phe Gly Asn
                805                 810                 815

Gly Asp Pro Pro Glu Asn Gly Glu Lys Phe Gly Cys Ala Leu Met Glu
            820                 825                 830

Met Arg His Pro Asn Ser Val Gln Glu Glu Arg Lys Ser Tyr Lys Val
            835                 840                 845

Arg Phe Asn Ser Val Ser Ser Tyr Ser Asp Ser Gln Lys Ser Ser Gly
        850                 855                 860

Asp Gly Pro Asp Leu Arg Asp Asn Phe Glu Ser Ala Gly Pro Leu Ala
865                 870                 875                 880

Asn Val Arg Phe Ser Val Phe Gly Leu Gly Ser Arg Ala Tyr Pro His
                885                 890                 895

Phe Cys Ala Phe Gly His Ala Val Asp Thr Leu Leu Glu Glu Leu Gly
            900                 905                 910

Gly Glu Arg Ile Leu Lys Met Arg Glu Gly Asp Glu Leu Cys Gly Gln
            915                 920                 925

Glu Glu Ala Phe Arg Thr Trp Ala Lys Lys Val Phe Lys Ala Ala Cys
        930                 935                 940

Asp Val Phe Cys Val Gly Asp Asp Val Asn Ile Glu Lys Ala Asn Asn
945                 950                 955                 960
```

```
Ser Leu Ile Ser Asn Asp Arg Ser Trp Lys Arg Asn Lys Phe Arg Leu
            965                 970                 975

Thr Phe Val Ala Glu Ala Pro Glu Leu Thr Gln Gly Leu Ser Asn Val
            980                 985                 990

His Lys Lys Arg Val Ser Ala Ala Arg Leu Leu Ser Arg Gln Asn Leu
            995                 1000                1005

Gln Ser Pro Lys Ser Ser Arg Ser Thr Ile Phe Val Arg Leu His
        1010                1015                1020

Thr Asn Gly Ser Gln Glu Leu Gln Tyr Gln Pro Gly Asp His Leu
        1025                1030                1035

Gly Val Phe Pro Gly Asn His Glu Asp Leu Val Asn Ala Leu Ile
        1040                1045                1050

Glu Arg Leu Glu Asp Ala Pro Pro Val Asn Gln Met Val Lys Val
        1055                1060                1065

Glu Leu Leu Glu Glu Arg Asn Thr Ala Leu Gly Val Ile Ser Asn
        1070                1075                1080

Trp Thr Asp Glu Leu Arg Leu Pro Pro Cys Thr Ile Phe Gln Ala
        1085                1090                1095

Phe Lys Tyr Tyr Leu Asp Ile Thr Thr Pro Pro Thr Pro Leu Gln
        1100                1105                1110

Leu Gln Gln Phe Ala Ser Leu Ala Thr Ser Glu Lys Glu Lys Gln
        1115                1120                1125

Arg Leu Leu Val Leu Ser Lys Gly Leu Gln Glu Tyr Glu Glu Trp
        1130                1135                1140

Lys Trp Gly Lys Asn Pro Thr Ile Val Glu Val Leu Glu Glu Phe
        1145                1150                1155

Pro Ser Ile Gln Met Pro Ala Thr Leu Leu Leu Thr Gln Leu Ser
        1160                1165                1170

Leu Leu Gln Pro Arg Tyr Tyr Ser Ile Ser Ser Ser Pro Asp Met
        1175                1180                1185

Tyr Pro Asp Glu Val His Leu Thr Val Ala Ile Val Ser Tyr Arg
        1190                1195                1200

Thr Arg Asp Gly Glu Gly Pro Ile His His Gly Val Cys Ser Ser
        1205                1210                1215

Trp Leu Asn Arg Ile Gln Ala Asp Glu Leu Val Pro Cys Phe Val
        1220                1225                1230

Arg Gly Ala Pro Ser Phe His Leu Pro Arg Asn Pro Gln Val Pro
        1235                1240                1245

Cys Ile Leu Val Gly Pro Gly Thr Gly Ile Ala Pro Phe Arg Ser
        1250                1255                1260

Phe Trp Gln Gln Arg Gln Phe Asp Ile Gln His Lys Gly Met Asn
        1265                1270                1275

Pro Cys Pro Met Val Leu Val Phe Gly Cys Arg Gln Ser Lys Ile
        1280                1285                1290

Asp His Ile Tyr Arg Glu Glu Thr Leu Gln Ala Lys Asn Lys Gly
        1295                1300                1305

Val Phe Arg Glu Leu Tyr Thr Ala Tyr Ser Arg Glu Pro Asp Lys
        1310                1315                1320

Pro Lys Lys Tyr Val Gln Asp Ile Leu Gln Glu Gln Leu Ala Glu
        1325                1330                1335

Ser Val Tyr Arg Ala Leu Lys Glu Gln Gly Gly His Ile Tyr Val
        1340                1345                1350
```

-continued

| Cys | Gly | Asp | Val | Thr | Met | Ala | Ala | Asp | Val | Leu | Lys | Ala | Ile | Gln |
|     | 1355 |     |     |     | 1360 |     |     |     |     | 1365 |     |     |     |     |

| Arg | Ile | Met | Thr | Gln | Gln | Gly | Lys | Leu | Ser | Ala | Glu | Asp | Ala | Gly |
| 1370 |     |     |     |     | 1375 |     |     |     |     | 1380 |     |     |     |     |

| Val | Phe | Ile | Ser | Arg | Met | Arg | Asp | Asp | Asn | Arg | Tyr | His | Glu | Asp |
|     | 1385 |     |     |     | 1390 |     |     |     |     | 1395 |     |     |     |     |

| Ile | Phe | Gly | Val | Thr | Leu | Arg | Thr | Tyr | Glu | Val | Thr | Asn | Arg | Leu |
| 1400 |     |     |     |     | 1405 |     |     |     |     | 1410 |     |     |     |     |

| Arg | Ser | Glu | Ser | Ile | Ala | Phe | Ile | Glu | Glu | Ser | Lys | Lys | Asp | Thr |
| 1415 |     |     |     |     | 1420 |     |     |     |     | 1425 |     |     |     |     |

| Asp | Glu | Val | Phe | Ser | Ser |
|     | 1430 |     |     |     |     |

<210> SEQ ID NO 2
<211> LENGTH: 12189
<212> TYPE: DNA
<213> ORGANISM: Homo sapiens

<400> SEQUENCE: 2

```
ataaaagatg tatgctttgg agcccagagc ggctctttta atgagggttg cgacgtctcc     60
ctccccacac cctaaaacca gtcgggttgg acgtcactgc taattcgttt cagtgatgat    120
aggataaagg agggacatta agaaataaat tcccccctcac gaccctcgct gagctcacgg   180
ctcagtccct acatatttat gccgcgtttc cagccgctgg gtgaggagct acttagcgcc    240
gcggctcctc cgaggggcgg ccgggcagcg agcagcggcc gagcggacgg gctcatgatg    300
cctcagatct gatccgcatc taacaggctg caatgaaga tacccagaga atagttcaca     360
tctatcatgc gtcacttcta gacacagcca tcagacgcat ctcctcccct ttctgcctga    420
ccttagggac acgtcccacc gcctctcttg acgtctgcct ggtcaaccat cacttcctta    480
gagaataagg agagaggcgg atgcaggaaa tcatgccacc gacgggccac cagccatgag    540
tgggtgacgc tgagctgacg tcaaagacag agagggctga agccttgtca gcacctgtca    600
ccccggctcc tgctctccgt gtagcctgaa gcctggatcc tcctggtgaa atcatcttgg    660
cctgatagca ttgtgaggtc ttcagacagg acccctcgga agctagttac catggaggat    720
cacatgttcg gtgttcagca aatccagccc aatgtcattt ctgttcgtct cttcaagcgc    780
aaagttgggg gctgggatt tctggtgaag gagcgggtca gtaagccgcc cgtgatcatc    840
tctgacctga ttcgtggggg cgccgcagag cagagtggcc tcatccaggc cggagacatc    900
attcttgcgg tcaacggccg gcccttggtg gacctgagct atgacagcgc cctggaggta    960
ctcagaggca ttgcctctga gacccacgtg gtcctcattc tgagggcccc tgaaggtttc   1020
accacgcacc tggagaccac ctttacaggt gatgggaccc ccaagaccat ccgggtgaca   1080
cagcccctgg gtcccccac aaagccgtg gatctgtccc accagccacc ggccggcaaa    1140
gaacagcccc tggcagtgga tggggcctcg ggtcccggga tgggcctca gcatgcctac    1200
gatgatgggc aggaggctgg ctcactcccc catgccaacg gcctggcccc caggccccca   1260
ggccaggacc ccgcgaagaa agcaaccaga gtcagcctcc aaggcagagg ggagaacaat   1320
gaactgctca aggagataga gcctgtgctg agccttctca ccagtgggag cagaggggtc   1380
aagggagggg cacctgccaa ggcagagatg aaagatatgg aatccaggt ggacagagat    1440
ttggacggca agtcacacaa acctctgccc ctcggcgtgg agaacgaccg agtcttcaat   1500
gacctatggg ggaagggcaa tgtgcctgtc gtcctcaaca cccatattc agagaaggag   1560
cagcccccca cctcaggaaa acagtccccc acaaagaatg gcagcccctc caagtgtcca   1620
```

```
cgcttcctca aggtcaagaa ctgggagact gaggtggttc tcactgacac cctccacctt    1680
aagagcacat tggaaacggg atgcactgag tacatctgca tgggctccat catgcatcct    1740
tctcagcatg caaggaggcc tgaagacgtc cgcacaaaag acagctctt  ccctctcgcc    1800 aaagagttta ttgatcaata ctattcatca attaaaagat ttggctccaa agcccacatg    1860
gaaaggctgg aagaggtgaa caaagagatc gacaccacta gcacttacca gctcaaggac    1920
acagagctca tctatggggc caagcacgcc tggcggaatg cctcgcgctg tgtgggcagg    1980
atccagtggt ccaagctgca ggtattcgat gcccgtgact gcaccacggc ccacgggatg    2040
ttcaactaca tctgtaacca tgtcaagtat gccaccaaca aagggaacct caggtctgcc    2100
atcaccatat tcccccagag gacagacggc aagcacgact tccgagtctg aactcccag    2160 ctcatccgct acgctggcta caagcagcct gacggctcca ccctggggga cccagccaat    2220
gtgcagttca cagagatatg catacagcag ggctggaaac cgcctagagg ccgcttcgat    2280
gtcctgccgc tcctgcttca ggccaacggc aatgaccctg agctcttcca gattcctcca    2340
gagctggtgt tggaagttcc catcaggcac cccaagtttg agtggttcaa ggacctgggg    2400
ctgaagtggt acgcctcccc cgccgtgtcc aacatgctcc tagagattgg cggcctggag    2460
ttcagcgcct gtccccttcag tggctggtac atgggcacag agattggtgt ccgcgactac    2520
tgtgacaact cccgctacaa tatcctggag gaagtggcca agaagatgaa cttagacatg    2580
aggaagacgt cctccctgtg aaggaccag gcgctggtgg agatcaatat cgcggttctc    2640
tatagcttcc agagtgacaa agtgaccatt gttgaccatc actccgccac cgagtccttc    2700
attaagcaca tggagaatga gtaccgctgc cgggggggct gccctgccga ctgggtgtgg    2760
atcgtgcccc ccatgtccgg aagcatcacc cctgtgttcc accaggagat gctcaactac    2820
cggctcaccc cctccttcga ataccagcct gatccctgga cacgcatgt  ctggaaaggc    2880 accaacggga cccccacaaa gcggcgagcc attggcttca agaagctagc agaagctgtc    2940
aagttctcgg ccaagctgat ggggcaggct atggccaaga gggtgaaagc gaccatcctc    3000
tatgccacag agacaggcaa atcgcaagct tatgccaaga ccttgtgtga gatcttcaaa    3060
cacgcctttg atgccaaggt gatgtccatg aagaatatg  acattgtgca cctggaacat    3120
gaaactctgg tccttgtggt caccagcacc tttggcaatg agatcccccc tgagaatggg    3180
gagaaattcg gctgtgcttt tgatggaatg aggcacccca actctgtgca ggaagaaagg    3240
aagagctaca aggtccgatt caacagcgtc tcctcctact ctgactccca aaaatcatca    3300
ggcgatgggc ccgacctcag agacaacttt gagagtgctg accccctggc caatgtgagg    3360
ttctcagttt ttggcctcgg ctcacgagca taccctcact tttgcgcctt cggacacgct    3420
gtggacaccc tcctggaaga actgggaggg gagaggatcc tgaagatgag ggaagggat    3480 gagctctgtg ggcaggaaga ggcttttcagg acctgggcca agaaggtctt caaggcagcc    3540
tgtgatgtct tctgtgtggg agatgatgtc aacattgaaa aggccaacaa ttccctcatc    3600
agcaatgatc gcagctggaa gagaaacaag ttccgcctca cctttgtggc cgaagctcca    3660
gaactcacac aaggtctatc caatgtccac aaaaagcgag tctcagctgc ccggctcctt    3720
agccgtcaaa acctccagag ccctaaatcc agtcggtcaa ctatcttcgt gcgtctccac    3780
accaacggga gccaggagct gcagtaccag cctggggacc acctgggtgt cttccctggc    3840
aaccacgagg acctcgtgaa tgccctgatc gagcggctgg aggacgcgcc gcctgtcaac    3900
cagatggtga aagtggaact gctggaggag cggaacacgg ctttaggtgt catcagtaac    3960
```

```
tggacagacg agctccgcct cccgccctgc accatcttcc aggccttcaa gtactacctg    4020
gacatcacca cgccaccaac gcctctgcag ctgcagcagt ttgcctccct agctaccagc    4080
gagaaggaga agcagcgtct gctggtcctc agcaagggtt tgcaggagta cgaggaatgg    4140
aaatggggca agaaccccac catcgtggag gtgctggagg agttcccatc tatccagatg    4200
ccggccaccc tgctcctgac ccagctgtcc ctgctgcagc ccgctacta ttccatcagc    4260 tcctccccag acatgtaccc tgatgaagtg cacctcactg tggccatcgt ttcctaccgc    4320
actcgagatg gagaaggacc aattcaccac ggcgtatgct cctcctggct caaccggata    4380
caggctgacg aactggtccc ctgtttcgtg agaggagcac ccagcttcca cctgccccgg    4440 aaccccaag tcccctgcat cctcgttgga ccaggcaccg gcattgcccc tttccgaagc    4500
ttctggcaac agcggcaatt tgatatccaa cacaaaggaa tgaaccctg ccccatggtc    4560 ctggtcttcg ggtgccggca atccaagata gatcatatct acagggaaga gaccctgcag    4620
gccaagaaca aggggtctt cagagagctg tacacggctt actcccggga gccagacaaa    4680
ccaaagaagt acgtgcagga catcctgcag gagcagctgg cggagtctgt gtaccgagcc    4740
ctgaaggagc aagggggcca catatacgtc tgtgggacg tcaccatggc tgctgatgtc    4800
ctcaaagcca tccagcgcat catgacccag caggggaagc tctcggcaga ggacgccggc    4860
gtattcatca gccggatgag ggatgacaac cgataccatg aggatatttt tggagtcacc    4920
ctgcgaacgt acgaagtgac caaccgcctt agatctgagt ccattgcctt cattgaagag    4980
agcaaaaaag acaccgatga ggttttcagc tcctaactgg accctcttgc ccagccggct    5040
gcaagttttg taagcgcgga cagacactgc tgaacctttc ctctgggacc ccctgtggcc    5100
ctcgctctgc ctcctgtcct tgtcgctgtg ccctggtttc cctcctcggg cttctcgccc    5160
ctcagtggtt tcctcggccc tcctgggttt actccttgag ttttcctgct gcgatgcaat    5220
gcttttctaa tctgcagtgg ctcttacaaa actctgttcc cactccctct cttgccgaca    5280
agggcaactc acgggtgcat gaaaccactg gaacatggcc gtcgctgtgg gggttttttt    5340
ctctggggtt cccctggaaa ggctgcagga actaggcaca agctctctga ccagtccct    5400 cagccactga agtccccctt tctccttttt tatgatgaca ttttggttgt gcgtgcctgt    5460
gtgtgtgtgt gtgtgtgtgt gtgtgtgtgt gatgggccag gtctctgtcc gtcctcttcc    5520
ctgcacaagt gtgtcgatct tagattgcca ctgctttcat tgaagaccct caatgccaag    5580
aaacgtgtcc ctggcccata ttaatccctc gtgtgtccat aattagggtc cacgcccatg    5640
tacctgaaac atttggaagc cccataattg ttctagttag aaagggttca gggcatgggg    5700
agaggagtgg gaaattgatt aaaggggctg tctcccaatg aaagaggcat tcccagaatt    5760
tgctgcattt agatttttgat accagtgagc agagccctca tgtgacatga acccatccaa    5820
tggattgtgc aaatcccctc cccaaaccca cccataccag ctagaatcac ttgactttgc    5880
cacatccatt gactgacccc ctcctccagc aatagcatcc aaggggcctg gaagttatgt    5940
tgttcaaaga agcctggtgg caataaggat cttcccactt tgccactgga tgactttgga    6000
tgggtcactt gtcctcagtt tttcctagtc ataatgtcat acgaacctaa agaatatgaa    6060
tggattaaat gttaaagctt tggtgcctgg aaacaatatc aagtaacaat atgattatta    6120 ttttttatt ccccaaagc gggcttgctg cttcacccctt ggggatgaaa taatggaagc    6180
tggttaaagt ggatgaggtt ggaaagagtt gccataatga ggtccacgt ggcttcttcg    6240 ataggagcca caacttgggg tgggaagaac ttgtccctca ggcttgttgc cctctgcagt    6300
tgatctccaa agttttaaac ctgttaaatt aattttgaca aataagttac cctcaactca    6360
```

```
gatcaaaaat gggcagccaa gtcttcggta ggaattggag ccggtgtaat tcctccctaa    6420
gaggcaacct gttgaattta ctctctcaga gtaaatggtg ggaagggatc cctttgtata    6480
cttttttaaa tactacaaat tagtgtcagg cagttcccag aaagagacaa gaaatcctag    6540
tggcctccca gactgcaggg tccccaagga tggaaaggga atgttctgct ggttctaccc    6600
tgtttgttgt gtcttgctat acagaaaaac cacatttctt ttatatactg tacgtgggca    6660
tatcttgttg ttcagtttgg gtgtctgcta aagaggaagt gcactggccc tctttgaaag    6720
ggctttacag tgggggcacc aagaccccaa agggcccagg ccaggagact gttaaagtga    6780
aaaggcaatc tatgactcac cttgctctgc catccctggc agcccccacc ggtgtcctgt    6840
tcctgccaca tggagcttga cttcatgcca gctataatct ccctgccctt cctttaatcc    6900
caatttcccc tgctcactct tccacagata taaagaacaa acacttagca tcccacactc    6960
accccttcta atcctgaagg gaagcccatt ctaaactcct ttcctgcaaa cccatttcca    7020
gctcctagta gctttcctcc caaaggcttt cttttccaatc ctttatagct ttggagacgc    7080
ctccccaatt ccccagggaa ggaaactgtt gtgtccaatc cccattaaag acaaattgat    7140
cagtgcttcc cactccaagt caagctttat gcaggaatgc ttttccatca gggaataaat    7200
acttagaagc gcttacaagg tgccaggcac ctccttttctg catgtgcctg cctttctagt    7260
agcagacaga tggaaacatt gtctcatttt gtcaaggagt ccaaagaaat gattataaaa    7320
ccaggattca tccttcttct ccagaaagat ttttttttaa gtaaacacct ttcaatcccc    7380
aacacaagct gcttcacaac tccaggctag aaggcaggag agcgatctga tgtgtttctt    7440
tcatttgcca gaattcctga taccaaaagc ctctctctct gttgagtaac ctctcaagga    7500
ccagagtgga gtccagattg ttaggctcag atcaagggtg gggaaatact gccctctcgt    7560
ggtggctttt catccaggcc tcgtagccaa ccgtttaagt gcaaatagaa attaagcaat    7620
gggtaagcaa aatagggttg acaagatatt tgggggttat tcgggttatg gcccatttat    7680
ttccctcttc cccctgaatt gaccagtagc agctccagcc ccatttcaca aaagtgagtt    7740
tggccaggag gaatgagacg tctcctgaaa taggaacacc ggaacatcat gctcacctgc    7800
catcactatg catccagttc ccacagcttg tgtcgtgaaa gagcagagag atgatgttaa    7860
actccttggg aggagagagg gcttctttttg gtttccctgg agtgagacag ccaggtgtct    7920
ttcttttgcg gggggacact tcagacccat caatatggaa ttttgggagc cgacctgagt    7980
gcaaatccta attctgcccc tgttggtgca gatggctgtg ggcggctcac ttgaccttttt    8040 agagtctgca tacccacctg tataacaagg tggattgaat gagacaatgc ccacgaaatg    8100
cccagttaca gtacctggtt caaaacttac tgcattttaa ttttttcactt aacttataac    8160 atgtcttgct tctccagtgt gtggaaggca ccgggcagtt tgcagagata agcaaaacac    8220
agttcctctc gtgcagaagg ttagaatcta tttttttttt tgacagagtc ttgctctgtc    8280
acccaggctg gcgtacagtg gtacgatctc agctcactgc atcctctgcc tccccagtt    8340 caagtgattc ttctgcctcg gcctcctgag taactgggac tacaggcgcc taccaccacg    8400
cccagctaag ttttgtattt ttagtagagt cagggtttca ccatgttggc caggctggtc    8460
ttgaattcct gacctcaaat gatccacgca cctcagcctc ccaaagtgct ggattacagg    8520
catgagccac cacgcccagc caaaggttat aatctgatgg agagagacac ccgtcttgga    8580
actgacataa atttctgggg tttgagaaat gggcggatt tcactggtag cttctggaag    8640
gtaagagttg tccaggaatt gggaagagtg agaggaaagg cacggacagg gagcatgtaa    8700
```

-continued

```
gataaattga ggctggcttt ggaaggctga ggagggtgag aaaaggtggg ctgggaccag      8760
accgtgggga gaggtgagtg gcattacaag aaatttaggc tttattcaga aggcaacagg      8820
gagtccctaa gaatgttttt caaaaaggga cattaaggcg attggagtta tacttggaaa      8880
agaaagttct ggccacagta cagagcatgg cccgttgagc tgttgggggg gttattgctg      8940
caaccaaggc ttgagtgagg gaagaggcgg atgtagtgat aaagagactc caggaactga      9000
atcagcgtac ctggcacccc atccattgta gagggtgaga ataaaggaga aattaaagca      9060
tcttgcaggc tgggcgcggt agctcatgtc tgtaatccca gcactttggg aggccgaggt      9120
gggtgtatca gttgaggtca ggagttggag accagtcagc cagttagtag aaaccctgac      9180
tctactaaga aaatacaaaa attagctggg catggtggca tgcgcctgta gtctcagcta      9240
cctgggaggc tgaggaagga ggatcgcttg agcccaggag gtggaggctg cagtgagcca      9300
agattgtacc actgcactcc agcctgggtg acagagcaag actcttatct caaaaaaaat      9360
aaaataaaat aaaataaaat aaacatcttc gccctagct gagagagagg tctctgaaga       9420
gcaggctcag ggaaaagatg agttttcaga gctgatgtga tagtcagctt ctctggagtc      9480
aacagggtga atccttccca agtccagcca tgcccagatg cccggaggga aaactgaccc      9540
ccagccagta gacattggct aagaacacag aatcttctga ccaaacacgc tttcagcagc      9600
tgcctgctct ggactttgaa agaggtcagg tcttgcccta agctcaaaac aagtgagagg      9660
tgtcctgacc tagctcatag ggcaaatggt cctaatagga tgggcaatcc agatgcctga      9720
gccccttcac tccgacagca ccagcgccta atgcagcctt tcattcttg ccattaggaa        9780 atctgtggac ttctagcctg tgttttaaac cagccatgtt tccttgtata tttccctacc      9840
cgctgcccca catcccagc atgccgctgt ggccaccatg tcctcaaagc cttctgtctg        9900
tatcaggaat gtagtctgag actgccagga agcaacaagg agagagaaac actaactagt      9960
cttcctttat aacccattca tactctctgg ctgtccccaa ccttcatagt ctcctgcatc     10020
caaatgtcct ctttggctca aaagtaggc caggcatggt ggttcatgcc tgtaatagca      10080
ctttgggaga ctgaggtggg aggatcactt ggggccagga gtttgagacc agcttgggca     10140
acacagcgca atctcgtctc tactaaaaaa aaaaaaaaa aaaaattagc tgggcatgat      10200
ggcatgctcc tgtggtccca gctacttggg aggctgaggc aggaggatca cttggtccca     10260
ggagtttgag gcgacagtga gctaggatcg caccactgca ctccagcctg agtgacagag     10320
caagaccctg tctctaaaaa aaattaaaat gaaagaccag gtgctgggat taaggaaaca     10380
caggtctgag ggtctgaggg aaggggcctg cctcccaggg agtcaacata gatgttcccc     10440
atgaacaggg atttgacttt ggaggccaac ctggcctggc ctctgccctt tatctcacac     10500
tccctatcct tggcccactg ccagtccctg ccttgtggca aaggggcccc aaaagaaaag     10560
ctgcccttcc ccaaatgtaa ggacccaggt acactttcac ccgtggaaag cagtgtctgt     10620
cgagagtctg tttcctatta atacttatca aagccatgtg cgagggaggt ggtcagctgt     10680
caatatgcct tagtatgttt atatgagttt gtttgtttct aaaatacccca aacagttctg    10740 gtcaagcggg gctatgcccg tctggcccaa aacacagtcc gttattaacg agatggccct     10800
ggcaggcggg aacaaatctg cctccatgca ctgcttcctg tagtcttttta gaaagtaact    10860 ccaggacatc gaagtgccca gatttgactc ctaagttcta ggagactgta gcgcagggtc     10920
tgtcaacctt agcactattg gcatttgggg ctgggtaatt cttctttgtg gggccgtcct     10980
tgggtactgt aggaagctga gcagcattcc tggcctccat ccacaagata cctgtagcag     11040
tgtcctgcca acggtaacaa tcaagtatgt catcagacat tgcccaatgt ccccaggggg     11100
```

-continued

```
caacacccct ctcttggact tcagggtcaa gagaatctct gctggctacc ccaggacttc    11160
tcattataga tttcctggag cacgcagcag aaactttgcc tagcccagtg gttgtttcca    11220
ttatctgctg ccaaagtggg atttgagggt gtccggggga gggggcatgg ggagggcagt    11280
atgctttcaa aaacccctcc caggccaggc gtggtggctc atgcctgtaa tcacaggact    11340
ttgggaggcc gaggctggca gatcacttga ggctgggagt tagagaccaa cctggctaac    11400
atggcaaaac ctcgtctcta ctaaaaatac aaaaatcagc ccggcgtggt ggcgggcatc    11460
tgtaatccca tctactcggg aggctgaggc aggagaatta cttgaaccca ggaggcagag    11520
gctgcagtga gccgagatgg caccactgca ctccagcttg ttgacagaat gagaccctgt    11580
ggaaaaaaaa aaaaaagccc tcccatgcca gaacagagga tggcagtctg tttcaataag    11640
acactgtgtc cttggtgttg gttctgatta agactcactg agatccagtg ctcttgagct    11700
gggtctcagt cccctcccat gtcctgtgct ctgccgccac tgttttcatt gttgtgttct    11760
cgttgtgatt gttaagactc acactcctgg ctcagcagtg gttttccaga aggcccaaag    11820
agcggtgccg ggcacccac gtcgcagtgt ccgttccggg cttgggaagc tggggaggtg    11880
ggcagacctg gtcgcatctc accacacaca cacacacaca cacacacaca cacgctgtca    11940
gaaactcggc cgtcccccct acctctgagc tctcaatgct gctaatctct gccaagtgtc    12000
cctgtgctcc agcaccttcc ttgaaggact gacgcccacc ccacgctctt tgcgaggttg    12060
tccaggctgt gtttgtcgca tgctcttctt ctgtatagtt ctcatcttcc aattttatgg    12120
gattcaacaa aagcctatta tgcttgtttg cattatggtt acaatattaa aaagtggatt    12180
caaaaaaaa                                                           12189
```

METHODS OF MEASURING LEVELS OF PHOSPHORYLATED NEURONAL NITRIC OXIDE SYNTHASE

CROSS-REFERENCE TO RELATED APPLICATIONS

This application is a 35 U.S.C. §371 U.S. national entry of International Application PCT/US2012/068425, having an international filing date of Dec. 7, 2012, which claims the benefit of U.S. Provisional Application No. 61/567,882, filed Dec. 7, 2011, and U.S. Provisional Application No. 61/668,654, filed Jul. 6, 2012, the content of each of the aforementioned applications is herein incorporated by reference in their entirety.

FIELD OF THE INVENTION

The present invention relates to the field of biomarkers. More specifically, the present invention relates to biomarkers useful in diagnosing brain injuries.

INCORPORATION-BY-REFERENCE OF MATERIAL SUBMITTED ELECTRONICALLY

This application contains a sequence listing. It has been submitted electronically via EFS-Web as an ASCII text file entitled "P12048-02_ST25.txt." The sequence listing is 28,706 bytes in size, and was created on Dec. 7, 2012. It is hereby incorporated by reference in its entirety.

BACKGROUND OF THE INVENTION

Brain injuries are complex and can have multiple severe clinical outcomes. Perinatal (fetal and neonatal) brain injury consists of a large group of conditions that produce mild to severe impairments in motor, visual, auditory and cognitive functions. Hearing loss affects 1 to 3 per 1000 normal newborns and 2 to 4 per 100 of infants who require neonatal intensive care. In the U.S., approximately 500,000 are born preterm each year. Children born preterm are at increased risk for adverse neurological outcomes, ranging from mild learning disabilities to cerebral palsy. Up to 23% of children born prior to 28 weeks of gestation develop cerebral palsy. Beyond perinatal brain injury, it is estimated by the Centers for Disease Control that 1.7 million people sustain traumatic brain injuries annually. With the current clinical tools, prognosis and therapies are limited.

Detection of brain injury is difficult, especially in fetuses and neonates with birth-related injury. Unfortunately, clinical tools such as physical exam, and imaging (CT Scan or MRI) are subjective, not widely available, not sensitive or specific enough and or too costly to identify the fetus or neonate with brain injury. Especially, it represents a challenge in premature infants where the developmental immaturity may mask the injury. There is a great clinical need to identify patients with brain injury because these fetuses and infants are at significant risk of progressing to neurological damage, learning problems and memory loss.

SUMMARY OF THE INVENTION

The present invention is based, at least in part, on the discovery that neuronal nitric oxide synthase (nNOS) increase and its phosphorylation status can be used as a marker for brain injury. More specifically, in certain embodiments, nNOS can be used as a marker for perinatal brain injury. In particular embodiments, the present invention provides an enzyme-linked immunosorbent assay (ELISA) to test for nNOS increase and/or its phosphorylation status.

Nitric oxide (NO) is biological messenger that plays an important role in the physiologic function of neurons within central as well as peripheral nervous system. Nitric oxide synthase (NOS) catalyzes the reaction that produces NO through oxidation of L-arginine in the presence of NADPH, oxygen, and five cofactors (FAD, FMN, calmodulin (CaM), tetrahydrobiopterin, and heme). There are three different isoforms of NOS: constitutive neuronal (nNOS) and endothelial (eNOS), and inducible (iNOS). eNOS is expressed in a variety of cell types, including vascular endothelial cells, cardiomyocytes, neutrophils, and epithelial cells of kidney and airways. iNOS is mainly produced by inflanunatory cells. nNOS is expressed in skeletal and cardiac myocytes, as well as in embryonic and adult neurons, where it acts as neurotransmitter. Whereas small quantities of NO are necessary during synaptic transmission, excess NO mediates neurotoxicity in pathological conditions, leading to neuronal death (1-3). This is believed to be a key mechanism of neurodegeneration as a result of excitotoxicity via N-methyl-D-aspartate receptors (NMDARs) and subsequent overproduction of nitric oxide via nNOS. As described herein, nNOS phosphorylation/dephosphorylation at Ser852 represents an important regulatory mechanism of nNOS activation, accomplished by CaM kinase 11 and phosphatases respectively.

In certain embodiments, the high levels of nNOS and its dephosphorylated stated (decrease in Phos-nNOS) is indicative of perinatal brain injury when identified in a sample including, but not limited to, amniotic fluid or a neonate's cord blood. By using an ELISA, in some embodiments, for the status of the marker (e.g., the level of nNOS and the level of Phos-nNOS), clinicians can determine brain injury levels for prognosis and early therapeutic interventions. The present invention can be used as a diagnostic (e.g., through and ELISA) to determine perinatal (fetal/neonatal) brain injury in fetuses and allow for earlier intervention thereby enhancing maternal and infant management.

Accordingly, in one aspect, the present invention provides methods and compositions for diagnosing brain injuries. In one embodiment, a method for diagnosing brain injury in a patient comprises the steps of (a) obtaining a sample from the patient; (b) determining the levels of phosphorylated neuronal nitric oxide synthase (nNOS) and unphosphorylated nNOS in the sample; and (c) correlating the levels to a patient having brain injury or to a patient not having brain injury, thereby providing the diagnosis. In particular embodiments, the sample is selected from the group consisting of amniotic fluid blood, cord blood, peripheral blood, serum, plasma, cerebrospinal fluid, urine, saliva, stool and synovial fluid. In more particular embodiments, the sample is amniotic fluid, blood, cord blood serum or plasma. In a specific embodiment, the sample is amniotic fluid. In another specific embodiment, the sample is cord blood. In yet another specific embodiment, the sample is serum. In a further embodiment, the sample is plasma.

In certain embodiments, the brain injury is perinatal brain injury. In particular embodiments, the determining step is accomplished using an immunoassay. In particular embodiments, the phosphorylated nNOS is phosphorylated at one or more serine, threonine, tyrosine or histidine amino acid residues. In specific embodiments, the phosphorylated nNOS is phosphorylated at one or more serine residues. In a specific embodiment, the phosphorylated nNOS is phosphorylated at Ser852.

In another embodiment, a method for diagnosing perinatal brain injury in a patient comprises the steps of (a) determining the levels of phosphorylated nNOS and unphosphorylated nNOS in a sample collected from the patient using an enzyme-linked immunosorbent assay; and (b) correlating the levels to a patient having perinatal brain injury or to a patient not having perinatal brain injury, thereby providing the diagnosis.

In yet another embodiment, a method for diagnosing perinatal brain injury in a patient comprises the steps of (a) measuring the levels of phosphorylated nNOS and unphosphorylated nNOS in a sample collected from the patient using an ELISA; and (b) comparing the levels with predefined levels of the same proteins that correlate to a patient having perinatal brain injury and predefined levels of the same proteins that correlate to a patient not having perinatal brain injury, wherein a correlation to one of the predefined ratios provides the diagnosis. In certain embodiments, the phosphorylated nNOS is phosphorylated at Ser852. In a further embodiment, a method for diagnosing perinatal brain injury in a patient comprises the steps of (a) obtaining a sample from a patient; (b) measuring the level of phosphorylated nNOS protein in the sample; and (c) correlating the level to a patient having perinatal brain injury or to a patient not having perinatal brain injury, thereby providing the diagnosis. In yet another embodiment, a method for diagnosing brain injury in a patient comprises the steps of (a) determining the level of phosphorylated nNOS in a sample collected from the patient using an ELISA; and (b) comparing the level with predefined phosphorylated nNOS levels that correlate to a patient having perinatal brain injury and predefined phosphorylated nNOS levels that correlate to a patient not having perinatal brain injury, wherein a correlation to one of the predefined levels provides the diagnosis. In a specific embodiment, a method for determining perinatal brain injury status in a patient comprises the steps of (a) collecting a sample from the patient; (b) measuring the level of phosphorylated nNOS and unphosphorylated nNOS; and (c) comparing the levels of phosphorylated nNOS and unphosphorylated nNOS with predefined levels that correlate to one or more perinatal brain injury statuses selected from the group consisting of having perinatal brain injury, not having perinatal brain injury, progressing perinatal brain injury, and regressing perinatal brain injury, wherein a correlation to one of the predefined levels determines the perinatal brain injury status of the patient. In such embodiments, the phosphorylated nNOS is phosphorylated at Ser852.

In another embodiment, a method for diagnosing brain injury in a patient comprises the steps of (a) obtaining a sample from the patient; (b) determining the ratio of phosphorylated neuronal nitric oxide synthase (nNOS) to unphosphorylated nNOS in the sample; and (c) correlating the ratio to a patient having brain injury or to a patient not having brain injury, thereby providing the diagnosis. In other embodiments, a method for diagnosing perinatal brain injury in a patient comprises the steps of (a) determining the ratio of phosphorylated nNOS to unphosphorylated nNOS in a sample collected from the patient using an enzyme-linked immunosorbent assay; and (b) correlating the ratio to a patient having perinatal brain injury or to a patient not having perinatal brain injury, thereby providing the diagnosis. Alternatively, a method for diagnosing perinatal brain injury in a patient comprises the steps of (a) determining the ratio of phosphorylated nNOS to unphosphorylated nNOS in a sample collected from the patient using an ELISA; and (b) comparing the ratio with predefined ratios of the same proteins that correlate to a patient having perinatal brain injury and predefined ratios of the same proteins that correlate to a patient not having perinatal brain injury, wherein a correlation to one of the predefined ratios provides the diagnosis. In such embodiments, phosphorylated nNOS is phosphorylated at Ser852.

In other embodiments, the present invention provides methods for treating brain injuries. In one embodiment, a method comprises the steps of (a) obtaining a sample from a patient suspected of having a brain injury; (b) measuring the level of phosphorylated nNOS protein in the sample using an ELISA; and (c) treating the patient for brain injury if the level of phosphorylated nNOS correlates to a patient having perinatal brain injury. In other embodiments, a method comprises the steps of (a) obtaining a sample from a patient suspected of having a brain injury; (b) determining the ratio of phosphorylated nNOS to unphosphorylated nNOS in the sample collected from a patient using an ELISA; and (c) treating the patient for brain injury if the ratio correlates to a patient having perinatal brain injury. In such embodiments, phosphorylated nNOS is phosphorylated at Ser852.

In another aspect, the present invention provides kits. A diagnostic kit for diagnosing brain injury in a patient can comprise (a) a substrate for collecting a biological sample from the patient; and (b) means for measuring the level of unphosphorylated nNOS and phosphorylated nNOS. In another embodiment, the phosphorylated nNOS is phosphorylated at Ser852.

BRIEF DESCRIPTION OF THE FIGURES

FIG. 3 shows human amniotic fluid studies Amniotic fluid was collected and processed per developed protocols in our laboratory.

DETAILED DESCRIPTION OF THE INVENTION

Figure 1A:
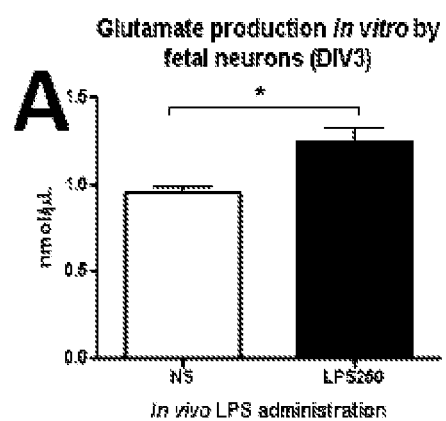
FIG. 1A shows primary cortical neuronal culture and whole brain analysis for excitotoxic pathways following in vivo exposure to intrauterine inflammation where glutamate production in vitro by fetal neurons (DIV3).

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. DEFINITIONS

The term "brain injury" refers to a condition in which the brain is damaged by injury caused by an event. As used herein, an "injury" is an alteration in cellular or molecular integrity, activity, level, robustness, state, or other alteration that is traceable to an event. For example, an injury includes a physical, mechanical, chemical, biological, functional, infectious, or other modulator of cellular or molecular characteristics. An event can include a physical trauma such as an impact (percussive) or a biological abnormality such as a stroke resulting from either blockade or leakage of a blood vessel. An event is optionally an infection by an infectious agent. A person of skill in the art recognizes numerous equivalent events that are encompassed by the terms injury or event.

More specifically, the term "brain injury" refers to a condition that results in central nervous system damage, irrespective of its pathophysiological basis. Among the most frequent origins of a "brain injury" are stroke and traumatic brain injury (TBI). A "stroke" is classified into hemorrhagic and non-hemorrhagic. Examples of hemorrhagic stroke include cerebral hemorrhage, subarachnoid hemorrhage, and intracranial hemorrhage secondary to cerebral arterial malformation, while examples of non-hemorrhagic stroke include cerebral infarction.

The term "perinatal brain injury" refers to brain injuries suffered by a fetus or a neonate.

The term "traumatic brain injury" or "TBI" refer to traumatic injuries to the brain which occur when physical trauma causes brain damage. For example, TBI can result from a closed head injury or a penetrating head injury. A "non-traumatic brain injury" refers to brain injuries that do not involve ischemia or external mechanical force (e.g., stroke, Alzheimer's disease, Parkinson's disease, Huntington's disease, multiple sclerosis, amyotrophic lateral sclerosis, brain hemorrhage, brain infections, brain tumor, among others).

The term "brain injury" also refers to subclinical brain injury, spinal cord injury, and anoxic-ischemic brain injury. The term "subclinical brain injury" (SCI) refers to brain injury without overt clinical evidence of brain injury. A lack of clinical evidence of brain injury when brain injury actually exists could result from degree of injury, type of injury, level of consciousness, medications particularly sedation and anesthesia.

The "spinal cord injury" refers to a condition in which the spinal cord receives compression/detrition due to a vertebral fracture or dislocation to cause dysfunction. As used herein, the term "anoxic-ischemic brain injury" refers to deprivation of oxygen supply to brain tissue resulting in compromised brain function and includes cerebral hypoxia. For example, anoxic-ischemic brain injury includes focal cerebral ischemia, global cerebral ischemia, hypoxic hypoxia (i.e., limited oxygen in the environment causes reduced brain function, such as with divers, aviators, mountain climbers, and fire fighters, all of whom are at risk for this kind of cerebral hypoxia), obstructions in the lungs (e.g., hypoxia resulting from choking, strangulation, the crushing of the windpipe).

The term "brain injury biomarker" (BIB), "brain injury biomarker protein", "brain injury biomarker peptide", brain injury biomarker polypeptide" and the like refer to a protein, including those described herein, that can be used in a method of the present invention, e.g., to diagnose brain injury in a patient. In certain embodiments, a brain injury biomarker includes neuronal nitric oxide synthase (nNOS). The term also includes other brain injury biomarker proteins known in the art. In addition, the term "brain injury biomarkers" also includes the isoforms and/or post-translationally modified forms of any of the foregoing. In particular embodiments, the post-translationally modification is phosphorylation of nNOS.

As used herein, the term "comparing" refers to making an assessment of how the proportion, level or cellular localization of one or more biomarkers in a sample from a patient relates to the proportion, level or cellular localization of the corresponding one or more biomarkers in a standard or control sample. For example, "comparing" may refer to assessing whether the proportion, level, or cellular localization of one or more biomarkers in a sample from a patient is the same as, more or less than, or different from the proportion, level, or cellular localization of the corresponding one or more biomarkers in standard or control sample. More specifically, the term may refer to assessing whether the proportion, level, or cellular localization of one or more biomarkers in a sample from a patient is the same as, more or less than, different from or otherwise corresponds (or not)

to the proportion, level, or cellular localization of predefined biomarker levels/ratios that correspond to, for example, a patient having brain injury, not having brain injury, is responding to treatment for brain injury, is not responding to treatment for brain injury, is/is not likely to respond to a particular brain injury treatment, or having/not having another disease or condition. In a specific embodiment, the term "comparing" refers to assessing whether the level of one or more biomarkers of the present invention in a sample from a patient is the same as, more or less than, different from other otherwise correspond (or not) to levels/ratios of the same biomarkers in a control sample (e.g., predefined levels/ratios that correlate to uninfected individuals, standard brain injury levels/ratios, etc.).

In another embodiment, the term "comparing" refers to making an assessment of how the proportion, level or cellular localization of one or more biomarkers in a sample from a patient relates to the proportion, level or cellular localization of another biomarker in the same sample. For example, a ratio of one biomarker to another from the same patient sample can be compared. In another embodiment, a level of one biomarker in a sample (e.g., a post-translationally modified biomarker protein) can be compared to the level of the same biomarker (e.g., unmodified biomarker protein) in the sample. In a specific embodiment, the proportion of phosphorylated nNOS biomarker protein (e.g., at Ser852) can be compared to the unmodified protein, both of which are measured in the same patient sample. Ratios of modified:unmodified biomarker proteins can be compared to other protein ratios in the same sample or to predefined reference or control ratios.

As used herein, the terms "indicates" or "correlates" (or "indicating" or "correlating," or "indication" or "correlation," depending on the context) in reference to a parameter, e.g., a modulated proportion, level, or cellular localization in a sample from a patient, may mean that the patient has a brain injury. In specific embodiments, the parameter may comprise the level of one or more biomarkers of the present invention. A particular set or pattern of the amounts of one or more biomarkers may indicate that a patient has a brain injury (i.e., correlates to a patient having brain injury). In other embodiments, a correlation could be the ratio of a post-translationally modified protein to the unmodified protein indicates (or a change in the ratio over time or as compared to a reference/control ratio) could mean that the patient has a brain injury). In specific embodiments, a correlation could be the ratio of phosphorylated nNOS (e.g., at Ser852) to the unphosphorylated form, or any other combination in which a change in one protein causes or is accompanied by a change in another.

In other embodiments, a particular set or pattern of the amounts of one or more biomarkers may be correlated to a patient being unaffected (i.e., indicates a patient does not have brain injury). In certain embodiments, "indicating," or "correlating," as used according to the present invention, may be by any linear or non-linear method of quantifying the relationship between levels/ratios of biomarkers to a standard, control or comparative value for the assessment of the diagnosis, prediction of brain injury or brain injury progression, assessment of efficacy of clinical treatment, identification of a patient that may respond to a particular treatment regime or pharmaceutical agent, monitoring of the progress of treatment, and in the context of a screening assay, for the identification of an anti-brain injury therapeutic.

The terms "patient," "individual," or "subject" are used interchangeably herein, and refer to a mammal, particularly, a human. The patient may have a mild, intermediate or severe disease or condition. The patient may be treatment naïve, responding to any form of treatment, or refractory. The patient may be an individual in need of treatment or in need of diagnosis based on particular symptoms or family history. In certain embodiments, the term patient refers to a fetus or a neonate. In some cases, the terms may refer to treatment in experimental animals, in veterinary application, and in the development of animal models for disease, including, but not limited to, rodents including mice, rats, and hamsters; and primates.

The terms "measuring" and "determining" are used interchangeably throughout, and refer to methods which include obtaining or providing a patient sample and/or detecting the level of a biomarker(s) in a sample. In one embodiment, the terms refer to obtaining or providing a patient sample and detecting the level of one or more biomarkers in the sample. In another embodiment, the terms "measuring" and "determining" mean detecting the level of one or more biomarkers in a patient sample. Measuring can be accomplished by methods known in the art and those further described herein. The term "measuring" is also used interchangeably throughout with the term "detecting."

The terms "sample," "patient sample," "biological sample," and the like, encompass a variety of sample types obtained from a patient, individual, or subject and can be used in a diagnostic or monitoring assay. The patient sample may be obtained from a healthy subject or a patient having symptoms associated with brain injury. Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, cord blood, amniotic fluid, cerebrospinal fluid, urine, saliva, stool and synovial fluid), solid tissue samples such as a biopsy specimen or tissue cultures or cells derived therefrom and the progeny thereof. In certain embodiments, a sample comprises amniotic fluid. In other embodiments, a sample comprises cerebrospinal fluid. In a specific embodiment, a sample comprises a blood sample. In another embodiment, a sample comprises a plasma sample. In yet another embodiment, a serum sample is used.

The definition of "sample" also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

An "antibody" is an immunoglobulin molecule that recognizes and specifically binds to a target, such as a protein, polypeptide, peptide, carbohydrate, polynucleotide, lipid, etc., through at least one antigen recognition site within the variable region of the immunoglobulin molecule. As used herein, the term is used in the broadest sense and encompasses intact polyclonal antibodies, intact monoclonal antibodies, antibody fragments (such as Fab, Fab', $F(ab')_2$, and Fv fragments), single chain Fv (scFv) mutants, multispecific antibodies such as bispecific antibodies generated from at least two intact antibodies, fusion proteins comprising an antibody portion, and any other modified immunoglobulin molecule comprising an antigen recognition site so long as the antibodies exhibit the desired biological activity. An antibody can be one of any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

As used herein, the terms "antibody fragments", "fragment", or "fragment thereof" refer to a portion of an intact antibody. Examples of antibody fragments include, but are not limited to, linear antibodies; single-chain antibody molecules; Fc or Fc' peptides, Fab and Fab fragments, and multispecific antibodies formed from antibody fragments. In most embodiments, the terms also refer to fragments that binding an antigen of a target molecule (e.g., nNOS) and can be referred to as "antigen-binding fragments."

As used herein, "humanized" forms of non-human (e.g., murine) antibodies are chimeric antibodies that contain minimal sequence, or no sequence, derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies can comprise residues that are not found in the recipient antibody or in the donor antibody. These modifications are generally made to further refine antibody performance. In general, the humanized antibody will comprise substantially all of at least one, and typically two, variable domains, in which all or substantially all of the hypervariable loops correspond to those of a nonhuman immunoglobulin and all or substantially all of the FR residues are those of a human immunoglobulin sequence. The humanized antibody can also comprise at least a portion of an immunoglobulin constant region (Fc), typically that of a human immunoglobulin. Examples of methods used to generate humanized antibodies are described in U.S. Pat. No. 5,225,539.

The term "human antibody" as used herein means an antibody produced by a human or an antibody having an amino acid sequence corresponding to an antibody produced by a human made using any of the techniques known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

"Hybrid antibodies" are immunoglobulin molecules in which pairs of heavy and light chains from antibodies with different antigenic determinant regions are assembled together so that two different epitopes or two different antigens can be recognized and bound by the resulting tetramer.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. An antigenic determinant can compete with the intact antigen (i.e., the "immunogen" used to elicit the immune response) for binding to an antibody.

The terms "specifically binds to," "specific for," and related grammatical variants refer to that binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M.

Various methodologies of the instant invention include a step that involves comparing a value, level, feature, characteristic, property, etc. to a "suitable control," referred to interchangeably herein as an "appropriate control," a "control sample," a "reference" or simply a "control." A "suitable control," "appropriate control," "control sample," "reference" or a "control" is any control or standard familiar to one of ordinary skill in the art useful for comparison purposes. In one embodiment, a "suitable control" or "appropriate control" is a value, level, feature, characteristic, property, etc., determined in a cell, organ, or patient, e.g., a control or normal cell, organ, or patient, exhibiting, for example, normal traits. For example, the biomarkers of the present invention may be assayed for levels/ratios in a sample from an unaffected individual (UI) or a normal control individual (NC) (both terms are used interchangeably herein). In another embodiment, a "suitable control" or "appropriate control" is a value, level, feature, characteristic, property, ratio, etc. determined prior to performing a therapy (e.g., a brain injury treatment) on a patient. In yet another embodiment, a transcription rate, mRNA level, translation rate, protein level/ratio, biological activity, cellular characteristic or property, genotype, phenotype, etc., can be determined prior to, during, or after administering a therapy into a cell, organ, or patient. In a further embodiment, a "suitable control" or "appropriate control" is a predefined value, level, feature, characteristic, property, ratio, etc. A "suitable control" can be a profile or pattern of levels/ratios of one or more biomarkers of the present invention that correlates to brain injury, to which a patient sample can be compared. The patient sample can also be compared to a negative control, i.e., a profile that correlates to not having brain injury.

II. DETECTION OF BRAIN INJURY BIOMARKERS

A. Detection by Immunoassay

In other embodiments, the biomarkers of the present invention can be detected and/or measured by immunoassay. Immunoassay requires biospecific capture reagents, such as antibodies, to capture the biomarkers. Many antibodies are available commercially. Antibodies also can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well-known in the art.

The present invention contemplates traditional immunoassays including, for example, sandwich immunoassays including ELISA or fluorescence-based immunoassays, immunoblots, Western Blots (WB), as well as other enzyme immunoassays. Nephelometry is an assay performed in liquid phase, in which antibodies are in solution. Binding of the antigen to the antibody results in changes in absorbance, which is measured. In a SELDI-based immunoassay, a biospecific capture reagent for the biomarker is attached to the surface of an MS probe, such as a pre-activated protein chip array. The biomarker is then specifically captured on the biochip through this reagent, and the captured biomarker is detected by mass spectrometry.

Although antibodies are useful because of their extensive characterization, any other suitable agent (e.g., a peptide, an aptamer, or a small organic molecule) that specifically binds a biomarker of the present invention is optionally used in place of the antibody in the above described immunoassays. For example, an aptamer that specifically binds all nNOS and/or one or more of its breakdown products might be used. Aptamers are nucleic acid-based molecules that bind specific ligands. Methods for making aptamers with a particular binding specificity are known as detailed in U.S. Pat. No. 5,475,096; U.S. Pat. No. 5,670,637; U.S. Pat. No. 5,696,249; U.S. Pat. No. 5,270,163; U.S. Pat. No. 5,707,796; U.S. Pat. No. 5,595,877; U.S. Pat. No. 5,660,985; U.S. Pat. No. 5,567,588; U.S. Pat. No. 5,683,867; U.S. Pat. No. 5,637,459; and U.S. Pat. No. 6,011,020.

B. Detection by Electrochemicaluminescent Assay

In several embodiments, the biomarker biomarkers of the present invention may be detected by means of an electrochemicaluminescent assay developed by Meso Scale Discovery (Gaithersrburg, Md.). Electrochemiluminescence detection uses labels that emit light when electrochemically stimulated. Background signals are minimal because the stimulation mechanism (electricity) is decoupled from the signal (light). Labels are stable, non-radioactive and offer a choice of convenient coupling chemistries. They emit light at ~620 nm, eliminating problems with color quenching. See U.S. Pat. No. 7,497,997; U.S. Pat. No. 7,491,540; U.S. Pat. No. 7,288,410; U.S. Pat. No. 7,036,946; U.S. Pat. No. 7,052,861; U.S. Pat. No. 6,977,722; U.S. Pat. No. 6,919,173; U.S. Pat. No. 6,673,533; U.S. Pat. No. 6,413,783; U.S. Pat. No. 6,362,011; U.S. Pat. No. 6,319,670; U.S. Pat. No. 6,207,369; U.S. Pat. No. 6,140,045; U.S. Pat. No. 6,090,545; and U.S. Pat. No. 5,866,434. See also U.S. Patent Applications Publication No. 2009/0170121; No. 2009/006339; No. 2009/0065357; No. 2006/0172340; No. 2006/0019319; No. 2005/0142033; No. 2005/0052646; No. 2004/0022677; No. 2003/0124572; No. 2003/0113713; No. 2003/0003460; No. 2002/0137234; No. 2002/0086335; and No. 2001/0021534.

C. Detection by Mass Spectrometry

In one aspect, the biomarkers of the present invention may be detected by mass spectrometry, a method that employs a mass spectrometer to detect gas phase ions. Examples of mass spectrometers are time-of-flight, magnetic sector, quadrupole filter, ion trap, ion cyclotron resonance, Orbitrap, hybrids or combinations of the foregoing, and the like.

In particular embodiments, the biomarkers of the present invention are detected using selected reaction monitoring (SRM) mass spectrometry techniques. Selected reaction monitoring (SRM) is a non-scanning mass spectrometry technique, performed on triple quadrupole-like instruments and in which collision-induced dissociation is used as a means to increase selectivity. In SRM experiments two mass analyzers are used as static mass filters, to monitor a particular fragment ion of a selected precursor ion. The specific pair of mass-over-charge (m/z) values associated to the precursor and fragment ions selected is referred to as a "transition" and can be written as parent m/z→fragment m/z (e.g. 673.5→534.3). Unlike common MS based proteomics, no mass spectra are recorded in a SRM analysis. Instead, the detector acts as counting device for the ions matching the selected transition thereby returning an intensity distribution over time. Multiple SRM transitions can be measured within the same experiment on the chromatographic time scale by rapidly toggling between the different precursor/fragment pairs (sometimes called multiple reaction monitoring, MRM). Typically, the triple quadrupole instrument cycles through a series of transitions and records the signal of each transition as a function of the elution time. The method allows for additional selectivity by monitoring the chromatographic coelution of multiple transitions for a given analyte. The terms SRM/MRM are occasionally used also to describe experiments conducted in mass spectrometers other than triple quadrupoles (e.g. in trapping instruments) where upon fragmentation of a specific precursor ion a narrow mass range is scanned in MS2 mode, centered on a fragment ion specific to the precursor of interest or in general in experiments where fragmentation in the collision cell is used as a means to increase selectivity. In this application the terms SRM and MRM or also SRM/MRM can be used interchangeably, since they both refer to the same mass spectrometer operating principle. As a matter of clarity, the term MRM is used throughout the text, but the term includes both SRM and MRM, as well as any analogous technique, such as e.g. highly-selective reaction monitoring, hSRM, LC-SRM or any other SRM/MRM-like or SRM/MRM-mimicking approaches performed on any type of mass spectrometer and/or, in which the peptides are fragmented using any other fragmentation method such as e.g. CAD (collision-activated dissociation (also known as CID or collision-induced dissociation), HCD (higher energy CID), ECD (electron capture dissociation), PD (photodissociation) or ETD (electron transfer dissociation).

In another specific embodiment, the mass spectrometric method comprises matrix assisted laser desorption/ionization time-of-flight (MALDI-TOF MS or MALDI-TOF). In another embodiment, method comprises MALDI-TOF tandem mass spectrometry (MALDI-TOF MS/MS). In yet another embodiment, mass spectrometry can be combined with another appropriate method(s) as may be contemplated by one of ordinary skill in the art. For example, MALDI-TOF can be utilized with trypsin digestion and tandem mass spectrometry as described herein.

In an alternative embodiment, the mass spectrometric technique comprises surface enhanced laser desorption and ionization or "SELDI," as described, for example, in U.S. Pat. No. 6,225,047 and U.S. Pat. No. 5,719,060. Briefly, SELDI refers to a method of desorption/ionization gas phase ion spectrometry (e.g. mass spectrometry) in which an analyte (here, one or more of the biomarkers) is captured on the surface of a SELDI mass spectrometry probe. There are several versions of SELDI that may be utilized including, but not limited to, Affinity Capture Mass Spectrometry (also called Surface-Enhanced Affinity Capture (SEAC)), and Surface-Enhanced Neat Desorption (SEND) which involves the use of probes comprising energy absorbing molecules that are chemically bound to the probe surface (SEND probe). Another SELDI method is called Surface-Enhanced Photolabile Attachment and Release (SEPAR), which involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker panel, pursuant to the present invention.

In another mass spectrometry method, the biomarkers can be first captured on a chromatographic resin having chromatographic properties that bind the biomarkers. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

D. Other Methods for Detecting Biomarkers

The biomarkers of the present invention can be detected by other suitable methods. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Furthermore, a sample may also be analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there. Protein biochips are biochips adapted for the capture of polypeptides. Many protein biochips are described in the art. These include, for example, protein biochips produced by Ciphergen Biosystems, Inc. (Fremont, Calif.), Invitrogen Corp. (Carlsbad, Calif.), Affymetrix, Inc. (Fremong, Calif.), Zyomyx (Hayward, Calif.), R&D Systems, Inc. (Minneapolis, Minn.), Biacore (Uppsala, Sweden) and Procognia (Berkshire, UK). Examples of such protein biochips are described in the following patents or published patent applications: U.S. Pat. No. 6,537,749; U.S. Pat. No. 6,329,209; U.S. Pat. No. 6,225,047; U.S. Pat. No. 5,242,828; PCT International Publication No. WO 00/56934; and PCT International Publication No. WO 03/048768.

III. DETERMINATION OF A PATIENT'S BRAIN INJURY STATUS

A. The present invention relates to the use of biomarkers to diagnose brain injury. More specifically, the biomarkers of the present invention can be used in diagnostic tests to determine, qualify, and/or assess brain injury or status, for example, to diagnose brain injury, in an individual, subject or patient. In particular embodiments, brain injury status can include determining a patient's brain injury status or brain injury status, for example, to diagnose brain injury, in an individual, subject or patient. More specifically, the biomarkers to be detected in diagnosing brain injury (e.g., perinatal brain injury) include, but are not limited to, neuronal nitric oxide synthase (nNOS). Other biomarkers known in the relevant art may be used in combination with the biomarkers described herein.

B. Biomarker Panels

The biomarkers of the present invention can be used in diagnostic tests to assess, determine, and/or qualify (used interchangeably herein) brain injury status in a patient. The phrase "brain injury status" includes any distinguishable manifestation of the condition, including not having brain injury. For example, brain injury status includes, without limitation, the presence or absence of brain injury in a patient, the risk of developing brain injury, the stage or severity of brain injury, the progress of brain injury (e.g., progress of brain injury over time) and the effectiveness or response to treatment of brain injury (e.g., clinical follow up and surveillance of brain injury after treatment). Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker panels of the present invention may show a statistical difference in different brain injury statuses of at least $p<0.05$, $p<10^{-2}$, $p<10^{-3}$, $p<10^{-4}$ or $p<10^{-5}$. Diagnostic tests that use these biomarkers may show an ROC of at least 0.6, at least about 0.7, at least about 0.8, or at least about 0.9.

The biomarkers can be differentially present in UI (NC or non-brain injury) and brain injury, and, therefore, are useful in aiding in the determination of brain injury status. In certain embodiments, the biomarkers are measured in a patient sample using the methods described herein and compared, for example, to predefined biomarker levels/ratios and correlated to brain injury status. In particular embodiments, the measurement(s) may then be compared with a relevant diagnostic amount(s), cut-off(s), or multivariate model scores that distinguish a positive brain injury status from a negative brain injury status. The diagnostic amount(s) represents a measured amount of a biomarker(s) above which or below which a patient is classified as having a particular brain injury status. For example, if the biomarker(s) is/are up-regulated compared to normal during brain injury, then a measured amount(s) above the diagnostic cutoff(s) provides a diagnosis of brain injury. Alternatively, if the biomarker(s) is/are down-regulated during brain injury, then a measured amount(s) at or below the diagnostic cutoff(s) provides a diagnosis of non-brain injury. As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of biomarkers in a statistically significant number of samples from patients with the different brain injury statuses, and drawing the cut-off to suit the desired levels of specificity and sensitivity.

In other embodiments, ratios of post-translationally modified biomarkers (e.g., phosphorylation of nNOS) to the corresponding unmodified biomarkers are useful in aiding in the determination of brain injury status. In certain embodiments, the biomarker ratios are indicative of diagnosis. In other embodiments, a biomarker ratio can be compared to another biomarker ratio in the same sample or to a set of biomarker ratios from a control or reference sample.

Indeed, as the skilled artisan will appreciate there are many ways to use the measurements of two or more biomarkers in order to improve the diagnostic question under investigation. In a quite simple, but nonetheless often effective approach, a positive result is assumed if a sample is positive for at least one of the markers investigated.

Furthermore, in certain embodiments, the values measured for markers of a biomarker panel are mathematically combined and the combined value is correlated to the underlying diagnostic question. Biomarker values may be combined by any appropriate state of the art mathematical method. Well-known mathematical methods for correlating a marker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present invention. In one embodiment, the method used in a correlating a biomarker combination of the present invention, e.g. to diagnose brain injury, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

C. Determining Risk of Developing Brain Injury

In a specific embodiment, the present invention provides methods for determining the risk of developing brain injury in a patient. Biomarker percentages, ratios, amounts or patterns are characteristic of various risk states, e.g., high, medium or low. The risk of developing brain injury is determined by measuring the relevant biomarker(s) and then either submitting them to a classification algorithm or comparing them with a reference amount, i.e., a predefined level or pattern of biomarker(s) that is associated with the particular risk level.

D. Determining Brain Injury Severity

In another embodiment, the present invention provides methods for determining the severity of brain injury in a patient. Each grade or stage of brain injury likely has a characteristic level of a biomarker or relative levels/ratios of a set of biomarkers (a pattern or ratio). The severity of brain injury is determined by measuring the relevant biomarker(s) and then either submitting them to a classification algorithm or comparing them with a reference amount, i.e., a predefined level or pattern of biomarker(s) that is associated with the particular stage.

E. Determining Brain injury Prognosis

In one embodiment, the present invention provides methods for determining the course of brain injury in a patient. Brain injury course refers to changes in brain injury status over time, including brain injury progression (worsening) and brain injury regression (improvement). Over time, the amount or relative amount (e.g., the pattern or ratio) of the biomarkers changes. For example, biomarker "X" may be increased with brain injury, while biomarker "Y" may be decreased with brain injury. Therefore, the trend of these biomarkers, either increased or decreased over time toward brain injury or non-brain injury indicates the course of the condition. Accordingly, this method involves measuring the level of one or more biomarkers in a patient at least two different time points, e.g., a first time and a second time, and comparing the change, if any. The course of brain injury is determined based on these comparisons.

F. Patient Management

In certain embodiments of the methods of qualifying brain injury status, the methods further comprise managing patient treatment based on the status. Such management includes the actions of the physician or clinician subsequent to determining brain injury status. For example, if a physician makes a diagnosis of brain injury, then a certain regime of monitoring would follow. An assessment of the course of brain injury using the methods of the present invention may then require a certain brain injury therapy regimen. Alternatively, a diagnosis of non-brain injury might be followed with further testing to determine a specific disease that the patient might be suffering from. Also, further tests may be called for if the diagnostic test gives an inconclusive result on brain injury status.

G. Determining Therapeutic Efficacy of Pharmaceutical Drug

In another embodiment, the present invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern, profile or ratio) of one or more of the biomarkers of the present invention may change toward a non-brain injury profile. Therefore, one can follow the course of one or more biomarkers in the patient during the course of treatment. Accordingly, this method involves measuring one or more biomarkers in a patient receiving drug therapy, and correlating the biomarker levels/ratios with the brain injury status of the patient (e.g., by comparison to predefined levels/ratios of the biomarkers that correspond to different brain injury statuses). One embodiment of this method involves determining the levels/ratios of one or more biomarkers for at least two different time points during a course of drug therapy, e.g., a first time and a second time, and comparing the change in levels/ratios of the biomarkers, if any. For example, the levels/ratios of one or more biomarkers can be measured before and after drug administration or at two different time points during drug administration. The effect of therapy is determined based on these comparisons. If a treatment is effective, then the level/ratio of one or more biomarkers will trend toward normal, while if treatment is ineffective, the level/ratio of one or more biomarkers will trend toward brain injury indications.

H. Generation of Classification Algorithms for Qualifying Brain Injury Status

In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition (e.g., diseased versus non-diseased).

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al. "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a UNIX, Windows® or Linux™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including R, C, C++, visual basic, etc.

The learning algorithms described above are useful both for developing classification algorithms for the biomarkers already discovered, and for finding new biomarker biomarkers. The classification algorithms, in turn, form the base for diagnostic tests by providing diagnostic values (e.g., cut-off points) for biomarkers used singly or in combination.

IV. KITS FOR THE DETECTION OF BRAIN INJURY BIOMARKERS

In another aspect, the present invention provides kits for qualifying brain injury status, which kits are used to detect the biomarkers described herein. In a specific embodiment, the kit is provided as an ELISA kit comprising antibodies to the biomarker(s) of the present invention. In a specific embodiment, the antibodies specifically bind to nNOS.

The ELISA kit may comprise a solid support, such as a chip, microtiter plate (e.g., a 96-well plate), bead, or resin having biomarker capture reagents attached thereon. The kit may further comprise a means for detecting the biomarker(s), such as antibodies, and a secondary antibody-signal complex such as horseradish peroxidase (HRP)-conjugated goat anti-rabbit IgG antibody and tetramethyl benzidine (TMB) as a substrate for HRP.

The kit for qualifying brain injury status may be provided as an immuno-chromatography strip comprising a membrane on which the antibodies are immobilized, and a means for detecting, e.g., gold particle bound antibodies, where the membrane, includes NC membrane and PVDF membrane. The kit may comprise a plastic plate on which a sample application pad, gold particle bound antibodies temporally immobilized on a glass fiber filter, a nitrocellulose membrane on which antibody bands and a secondary antibody band are immobilized and an absorbent pad are positioned in a serial manner, so as to keep continuous capillary flow of blood serum.

In certain embodiments, a patient can be diagnosed by adding blood or blood serum from the patient to the kit and detecting the relevant biomarker(s) conjugated with antibodies, specifically, by a method which comprises the steps of: (i) collecting blood or blood serum from the patient; (ii) separating blood serum from the patient's blood; (iii) adding the blood serum from patient to a diagnostic kit; and, (iv) detecting the biomarker(s) conjugated with antibodies. In this method, the antibodies are brought into contact with the patient's blood. If the biomarkers are present in the sample, the antibodies will bind to the sample, or a portion thereof. In other kit and diagnostic embodiments, blood or blood serum need not be collected from the patient (i.e., it is already collected). Moreover, in other embodiments, the sample may comprise a tissue sample or a clinical sample.

The kit can also comprise a washing solution or instructions for making a washing solution, in which the combination of the capture reagents and the washing solution allows capture of the biomarkers on the solid support for subsequent detection by, e.g., antibodies or mass spectrometry. In a further embodiment, a kit can comprise instructions for suitable operational parameters in the form of a label or separate insert. For example, the instructions may inform a consumer about how to collect the sample, how to wash the probe or the particular biomarkers to be detected, etc. In yet another embodiment, the kit can comprise one or more containers with biomarker samples, to be used as standard(s) for calibration.

V. NEURONAL NITRIC OXIDE SYNTHASE (nNOS) ANTIBODIES

In one aspect, the present invention provides antibodies to nNOS that are useful for diagnostic or screening purposes.

In certain embodiments, the antibodies described herein are isolated. In certain embodiments, the antibodies described herein are substantially pure.

In some embodiments the antibodies are monoclonal antibodies. In certain embodiments, the antibodies are chimeric, humanized, or human antibodies. The invention further provides bispecific antibodies. In certain embodiments, the antibodies are antibody fragments, such as Fab fragments.

In particular embodiments, the present invention provides isolated antibodies against nNOS. In a specific embodiment, the antibodies are specific for SEQ ID NO:1. In other embodiments, the antibodies specifically bind amino acid 852 of SEQ ID NO:1. In specific embodiments, the antibodies specifically bind phosphorylated Ser852 of SEQ ID NO:1. The antibody, or antibody fragment thereof, can be any monoclonal or polyclonal antibody that specifically recognizes nNOS. In some embodiments, the present invention provides monoclonal antibodies, or fragments thereof, that specifically bind to nNOS. In some embodiments, the monoclonal antibodies, or fragments thereof, are chimeric or humanized antibodies that specifically bind to nNOS or an eptiope or antigenic determinant thereof.

The antibodies against nNOS find use in the experimental and diagnostic methods described herein. In certain embodiments, the antibodies of the present invention are used to detect the expression of an nNOS protein in biological samples such as, for example, a tissue, blood, plasma, serum, cord blood, amniotic fluid, cerebrospinal fluid sample and the like. Tissue biopsies can be sectioned and nNOS protein detected using, for example, immunofluorescence or immunohistochemistry. Alternatively, individual cells from a sample are isolated, and protein expression detected on fixed or live cells by FACS analysis. Furthermore, the antibodies can be used on protein arrays to detect expression of nNOS, for example, on cells, in cell lysates, or in other protein samples.

Polyclonal antibodies can be prepared by any known method. Polyclonal antibodies can be raised by immunizing an animal (e.g., a rabbit, rat, mouse, donkey, etc) by multiple subcutaneous or intraperitoneal injections of the relevant antigen (a purified peptide fragment, full-length recombinant protein, fusion protein, etc) optionally conjugated to keyhole limpet hemocyanin (KLH), serum albumin, etc. diluted in sterile saline and combined with an adjuvant (e.g., Complete or Incomplete Freund's Adjuvant) to form a stable emulsion. The polyclonal antibody is then recovered from blood, ascites and the like, of an animal so immunized Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay such as radioimmunoassay (RIA) or enzyme-linked immunosorbent assay (ELISA) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated, such as from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different ways using recombinant DNA technology to generate alternative antibodies. In one embodiment, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity, affinity, etc. of a monoclonal antibody.

In some embodiments, of the present invention the monoclonal antibody against nNOS is a humanized antibody. Humanized antibodies are antibodies that contain minimal sequences from non-human (e.g., murine) antibodies within the variable regions. In practice, humanized antibodies are typically human antibodies with minimum to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDR of a human antibody with that of a non-human antibody (e.g., mouse, rat, rabbit, hamster, etc.) having the desired specificity, affinity, and capability (Jones et al., 1986, Nature, 321:522-525; Riechmann et al., 1988, Nature, 332:323-327; Verhoeyen et al., 1988, Science, 239: 1534-1536). The humanized antibody can be further modified by the substitution of additional residue either in the Fv framework region and/or within the replaced non-human residues to refine and optimize antibody specificity, affinity, and/or capability.

Human antibodies can be directly prepared using various techniques known in the art. Immortalized human B lymphocytes immunized in vitro or isolated from an immunized individual that produce an antibody directed against a target antigen can be generated (See, for example, Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373). Also, the human antibody can be selected from a phage library, where that phage library expresses human antibodies (Vaughan et al., 1996, Nature Biotechnology, 14:309-314; Sheets et al., 1998, PNAS, 95:6157-6162; Hoogenboom and Winter, 1991, J. Mol. Biol., 227:381; Marks et al., 1991, J. Mol. Biol., 222:581). Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In certain embodiments of the invention, it may be desirable to use an antibody fragment, rather than an intact antibody. Various techniques are known for the production of antibody fragments. Traditionally, these fragments are derived via proteolytic digestion of intact antibodies (for example Morimoto et al., 1993, Journal of Biochemical and Biophysical Methods 24:107-117 and Brennan et al., 1985, Science, 229:81). However, these fragments are now typically produced directly by recombinant host cells as described above. Thus Fab, Fv, and scFv antibody fragments can all be expressed in and secreted from E. coli or other host cells, thus allowing the production of large amounts of these fragments. Alternatively, such antibody fragments can be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent.

The present invention further embraces variants and equivalents which are substantially homologous to the chimeric, humanized and human antibodies, or antibody fragments thereof, set forth herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Neuronal Nitric Oxide Synthase (nNOS) in Maternal/Fetal Biological Fluid and Tissue as a Biomarker of Fetal Brain Injury Fetal inflammatory response syndrome (FIRS) associated with intrauterine inflammation, such as cases of preterm birth, preterm premature rupture of membranes and chorioamnionites and general cases of intraurine inflammation, is thought to be the mechanism that leads to a spectrum of neurobehavioral outcomes in affected children. Using a mouse model of intrauterine inflammation, the present invention demonstrates that neuroinflammation contributes to fetal neuronal injury and neuronal death follows an activation/phosphorylation of key components of the excitotoxic cascade, where there is an excess of glutamate, an excitatory neurotransmitter. There are currently no available diagnostic modalities to predict fetal/neonatal brain injury in the exposed fetuses. The phosphorylation of the markers of excitotoxic cascade expressed in the amniotic fluid (AF) cells can be used as an indicator of fetal brain injury. Any site on this enzyme that activates the enzyme by phosphorylation/dephosphorylation is within the scope of the present invention. The present invention is also directed to conducting AF studies utilizing a mouse model of intrauterine inflammation and inflammation-induced preterm birth and AF studies utilizing human samples in order to assess phosphorylation of a marker of excitatory cascade in presence and activation with intrauterine inflammation. This marker may be utilized for diagnostic stratification of fetuses/neonates and manage prevention/rescue from brain injury.

The present inventors conducted AF studies utilizing a mouse model of intrauterine inflammation and inflammation-induced preterm birth (II-PTB) and AF studies utilizing human samples in order to assess nNOS presence and activation with intrauterine inflammation.

The study design was as follows:
1. A mouse model of intrauterine inflammation and preterm birth was utilized (n=6 pregnant mice/group in LPS and normal saline groups).
2. Human AF samples from non-infected patients were utilized for investigation of nNOS. For mouse model, AF was prepared and tested for presence of nNOS and activation of nNOS in AF with Western blot analysis for phosphorylation at Serine 847. Human samples were tested for presence of knows by ELISA and for presence of the phosphorylated form of nNOS by confirmatory Western blot analysis.

Results

Murine studies demonstrate the presence of nNOS in the amniotic fluid, and an activation of this enzyme after exposure to intrauterine inflammation by Western blot analysis for the phosphorylated form (p<0.05). Ten human AF specimens (22-33.0 weeks of gestation) demonstrate presence of nNOS by ELISA and confirmatory tests with Western blot for the phosphorylated form of the enzyme.

Conclusion nNOS is activated with intrauterine inflammation in murine model and is present in human non-infected AF samples. nNOS may be an important in utero marker of fetal brain injury and may hold the key to the diagnosis of affected fetuses in utero, through an assessment of AF.

Figure 1B:
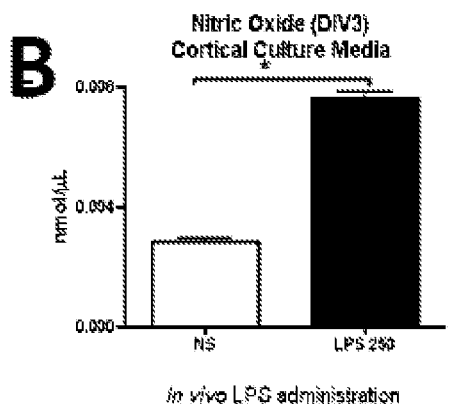
FIG. 1B shows primary cortical neuronal culture and whole brain analysis for excitotoxic pathways following in vivo exposure to intrauterine inflammation where nitric oxide (DIV3) production were increased.
Figure 1C:
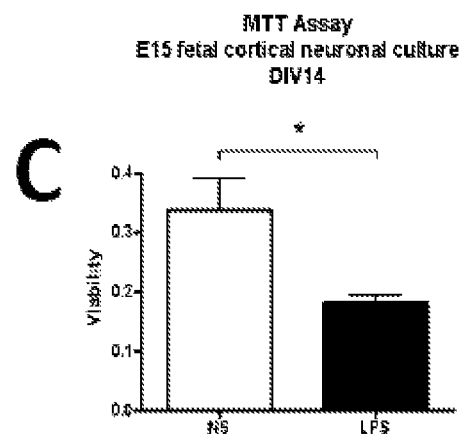
FIG. 1C shows primary cortical neuronal culture and whole brain analysis for excitotoxic pathways following in vivo exposure to intrauterine inflammation where MTT measurement shows a mitochondrial activity assay.
Figure 1D:
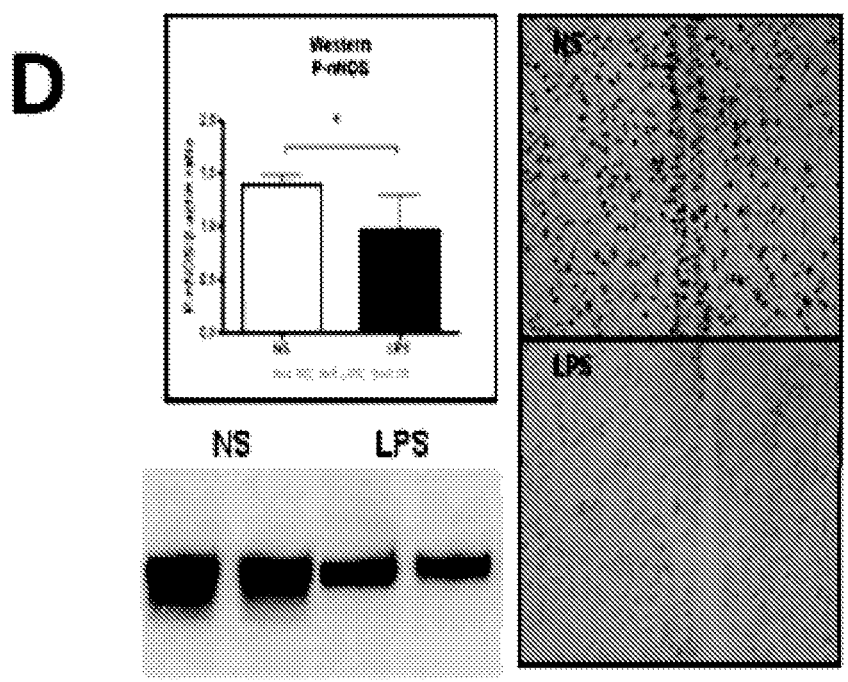
FIG. 1D shows primary cortical neuronal culture and whole brain analysis for excitotoxic pathways following in vivo exposure to intrauterine inflammation where using Western blot analysis shows analysis of fetal cortex (left panel) and immunohistochemistry of parasagittal cortex (right panel).

The overall hypothesis is that activation of nNOS in human amniotic fluid may be used as indicator of the development of fetal brain injury. The present inventors' prior work utilizing an animal model of a localized lipopolysaccharide (LPS; a component of the cell wall of Gram-negative bacteria) infusion into a murine uterus, has demonstrated that exposure to intrauterine inflammation leads to fetal neurotoxicity. This neurotoxicity has been shown to occur through excitatory mechanisms in FIGS. 1A through 1D which shows primary cortical neuronal culture and whole brain analysis for excitotoxic pathways following in vivo exposure to intrauterine inflammation. An increased activation of nNOS was identified (dephosphorylation at Serine 847; lessening of the amount of the phosphorylated form; FIG. 1D as part of the pathway leading to decreased neuronal viability (neurotoxicity); FIG. 1C. Lipopolysaccharide or normal saline (NS) was injected intrauterine (IU) (n=6-8 dams/group). Glutamate production as shown in FIG. 1A and nitric oxide production as shown in FIG. 1B production were increased in primary cortical neuronal cultures exposed to in vivo intrauterine inflammation. Cell viability as shown in FIG. 1C, as measured by MTT, a mitochondrial activity assay, was decreased at DIV 14 demonstrating a delayed neurotoxicity response. The studies of whole fetal brains 6 hours after injection demonstrated the activation of neuronal nitric oxide synthase (nNOS) by dephosphorylation at Serine 847. Both Western blot analysis of fetal cortex as shown in FIG. 1(d) (left panel) and immunohistochemistry of parasagittal cortex, as shown in FIG. 1(d) (right panel; 100×) demonstrated the decreased phosphorylated form of nNOS, indicating nNOS activation; *p<0.05.

Figure 2:
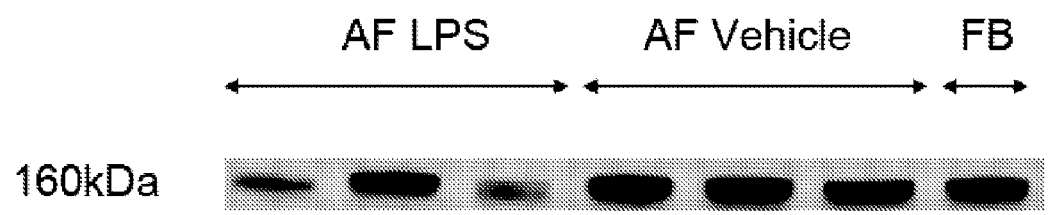
FIG. 2 shows murine amniotic fluid studies. Lipopolysaccharide or normal saline (vehicle) was injected intrauterine (n=6-8 dams/group) Amniotic fluid was collected from all gestational sacs in each injected dam 6 hours after initiation of intrauterine inflammation with lipopolysaccharide. Western blot analysis for phosphorylated nNOS on pooled vacuum-extracted pellets was performed (n=3/treatment group is depicted). In semi-quantitative analysis, where the respective amounts were calculated in reference to beta actin (control) and compared, there was a statistically significant difference (p=0.0224) between the treatment groups. Abbreviations: AF=amniotic fluid; LPS=lipopolysaccharide; FB=fetal brain (positive control for these studies); kDa=kilo Daltons.
Figure 3A:
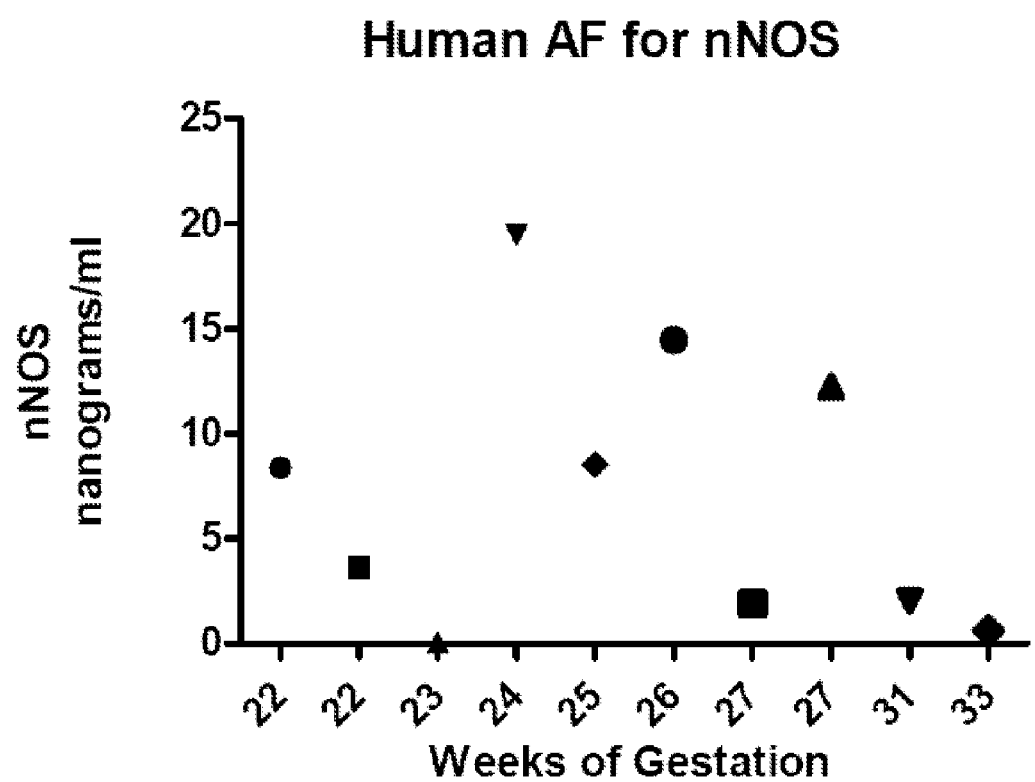
FIG. 3A shows ELISA studies for nNOS in non-infected AF samples, demonstrates variable amounts of nNOS (n=10).
Figure 3B:
FIG. 3B shows Confirmatory Western blot analysis for the phosphorylated form of nNOS on vacuum-extracted pellets were generated. Western blot analysis for nNOS was performed (n=6 is depicted). Western blots demonstrate presence of phosphorylated form of nNOS in the cell component fraction of the amniotic fluid.

Murine AF studies from the intrauterine inflammation model (LPS intrauterine infusion) demonstrate an activation of nNOS in pellets, vacuum extracted from AF pooled from all of the gestational sacs, specific to exposure to intrauterine inflammation as shown in FIG. 2; p<0.05). Laboratory work on 10 human AF samples demonstrate that nNOS is present at 22 to 33 weeks of gestation by ELISA (for detection of the enzyme) and by Western blot analysis, for the phosphorylated form of the enzyme as shown in FIG. 3; n=6 "non=affected pregnancies."

Example 2 nNOS in Cord Blood as a Marker of Neonatal Encephalopathy in Full Term Gestations Objective.

Currently, neonatal encephalopathy (a form of perinatal brain injury) is a clinical diagnosis, and there are no markers to diagnose or prognosticate the injury. The purpose of this study was to determine: 1) nNOS, a neuron-specific marker of oxidative stress, is present in cord blood of neonates; and 2) whether the level of nNOS differs in neonates with a clinical diagnosis of neonatal encephalopathy (NE) compared with neurologically normal neonates.

Methods.

This was a case-control study of full term neonates. Cases were neonates clinically diagnosed with moderate to severe NE at birth and underwent whole body cooling per institutional protocol. Controls were age-matched neurologically normal neonates. ELISA for nNOS was performed.

Results.

ELISA for nNOS was performed on 41 neonates (n=17 cases and n=24 controls). nNOS was present in neonatal cord blood. nNOS was significantly increased in NE cases (mean 1.19+/−0.86) compared with controls (mean 0.71+/−0.39; p<0.01). ROC curve yielded an area under the curve (AUC) of 0.734. Stringent criteria were applied to clinically encephalopathic neonates, and only those that had suffered a hypoxic-ischemic injury in utero (birth umbilical artery cord pH<7.0 and a base deficit of >12) were isolated to compare with neurologically normal neonates (cord pH>7.2, base deficit<8). The mean nNOS level was significantly increased in encephalopathic neonates who suffered hypoxic-ischemic injury in utero (mean 1.2+/−0.97, n=12) compared with neurologically normal neonates (mean 0.48+/−0.34, n=10) (p<0.05). ROC curve yielded an AUC=0.84 for prediction of abnormal neurologic status.

The data is summarized as follows:

1. nNOS and Phos-nNOS are detected in murine AF.
2. In the mouse model of intrauterine inflammation with a phenotype of perinatal brain injury in offspring, in utero exposure to intrauterine inflammation increased activation of nNOS (a decrease in Phos-nNOS) in murine AF.
3. nNOS and Phos-nNOS are detected in human AF samples from normal pregnancies.
4. nNOS and Phos-nNOS levels exhibit gestational differences in normal pregnancies.
5. nNOS and Phos-nNOS are present in cord blood of human neonates.
6. nNOS levels are increased in cord blood of newborns that suffered in utero hypoxic-ischemic injury and were found to have neonatal encephalopathy (a form of perinatal brain injury).

Conclusion

These studies indicate that nNOS is present in neonatal blood. nNOS is significantly elevated in neonates with perinatal brain injury and can serve as a marker for prognostication and therapeutic stratification.

Example 3

Enzyme-Linked Immunosorbent Assay (ELISA) of Phosphorylated at Ser 852 Neuronal NO Synthase While phosphorylation at Ser852 reduces nNOS activity by inhibiting CaM binding, dephosphorylation restores nNOS activity (4-6). As shown in the present inventors' research model of LPS-induced preterm birth in mice, there is an increase of phosphorylated nNOS at Ser852 in LPS-treated group versus PBS-treated group as revealed by molecular studies of sample tissues, including amniotic fluid (AF). Molecular analysis of AF during amniocentesis or cord blood for phosphorylation/dephosphorylation state at Ser852 may provide important diagnostic tool for preterm birth evaluation as far perinatal development of brain injury. This information is of crucial importance for therapy stratification.

ELISA Development.

The enzyme-linked immunosorbent assay (ELISA) has become a powerful method for measuring protein phosphorylation. ELISA has several advantages versus Western blot technique. First, the results are easily quantifiable and typical data represented by actual values determined by calibrated standard curve. Second, high specificity and sensitivity are possible due to the use of two antibodies specific for the target protein in the indirect, "sandwich" ELISA. Third, it is possible to use smaller sample volumes, and perform high throughput analysis in shorter time frame. The format for this microplate-based assay typically utilizes a capture antibody specific for the desired protein, independent of the phosphorylation state. The target protein, either purified or as a component in a complex heterogeneous sample such as a cell lysate, is then bound to the antibody-coated plate. A detection antibody specific for the phosphorylation site to be analyzed is then added. These assays are typically designed using colorimetric or fluorometric detection. The intensity of the resulting signal is directly proportional to the concentration of phosphorylated protein present in the original sample.

Commercially available ELISA kits are mostly designed for total target protein, independent of its phosphorylation/dephosphorylation state, which is the reason why the present inventors developed the present ELISA, specific for certain phosphorylation sites. One of the difficulties is to get purified and phosphorylated protein of interest at certain sites, which itself compose a challenge, while not guaranteeing hundred percent phosphorylation at desired site. In the case of human nNOS, the purified protein of human origin with tags for subsequent recovery from in vitro phosphorylation assay is not readily available on the market, making the production of own purified and phosphorylated standard protein tedious and expensive multistep procedure, while again not guaranteeing complete phosphorylation and not degraded protein. To circumvent this problem, different approaches were tried. First, there is possibility to run the same microplate using simultaneously the antibodies to total nNOS (pan-NOS) and to Ser852-phosphorylated nNOS (p-NOS). In this case one deals with relative values and normalized p-NOS/pan-NOS ratios. Disadvantage of this approach is the necessity to run control samples from microplate to microplate in order to compare results from different microplates, and operate with relative values. Another approach utilizes standard curve for total NOS, using commercially available purified nNOS from rat (94% homology with human nNOS). For human nNOS phosphorylated at Se852, the approach accomplished in ELISAs dealing with small molecules was used, namely commercially available phosphorylated at Ser852 peptide with sequence derived from human nNOS were used, which were labeled with biotin.

Results

ELISA, Normalized p-NOS/Pan-NOS Ratio.

Figure 4:
FIG. 4 is a graph showing pNOS/NOS ratio in AF of normal patients (n=14).

The results, obtained using this approach are shown in FIG. 4. Unlike ELISAs for phosphorylated target protein available from companies, the present inventors have found that coating of microplates with phospho-specific antibodies and probing with pan-NOS antibodies provides better results in terms of higher sensitivity and lower background. Briefly, clear polystyrene 96-well microplates were coated with 100 μl per well of pan-NOS and p-NOS antibodies overnight at 4° C. in the working concentration of 2.0 μl/ml in PBS without carrier protein. Each well was aspirated and wash with washing buffer using manifold dispenser for a total of 3 washes. Next, microplate was blocked with blocking buffer for 1-2 hours at room temperature. Aspiration and washing was repeated 3 times thereafter. 100 µl of samples were added in duplicates into wells coated with pan-NOS and p-NOS respectively, and incubated for 2 hours at room temperature. Aspiration and washing was repeated. Primary antibodies for pan-NOS and p-NOS were biotinylated according to manufacturer's protocol (Thermo Scientific). The detection antibody was diluted to a working concentration of 1 µg/ml for pan-NOS and of 2.5 µl/mg for p-NOS antibodies, respectively. Plate was sealed with a new plate sealer and incubated for 2 hours at room temperature. Aspiration and washing was repeated. Streptavidin-HRP was diluted to the working concentration (200 times dilution), added in the amount of 100 µl to each well, and incubated for 30 min. at room temperature. Aspiration and washing was repeated. 100 µl of substrate solution (TMB) was added to each well and incubated for 30 min. at room temperature. 50 µl of stop solution was added to each well. Optical density was determined immediately, using a microplate reader set to 450 nm absorbance. Readings from 540 nm were subtracted from readings at 450 nm. Blank readings were subtracted, and average for the duplicate readings for each sample was calculated. Phosphorylated/dephosphorylated at Ser 852 ratio was calculated for each sample and presented using GraphPadPrizm5 software. The results show the variation of phosphorylated at Ser852 human nNOS between 40-60% of total nNOS.

ELISA, Actual p-NOS/Pan-NOS Ratio.

In order to get standard curve and be able to calculate actual values for pan-NOS and p-NOS, two approaches were utilized. Because nNOS from rat is available and can be used for standard curve generation and quantification of human nNOS, the bigger problem is to get phosphorylated at Ser852 human nNOS. Instead of dealing with expensive multistep procedure of nNOS phosphorylation and subsequent recovery and purification, not guaranteeing hundred percent phosphorylation and not degraded protein at the end, the present inventors used phosphopeptide, corresponding to Ser852 phosphorylation site, which is inexpensive, commercially available, stable and easy to use peptide. First, this peptide can be used in the range of concentrations to coat the microplates, with subsequent probing with phospho-specific antibodies in the format of direct ELISA. The difficulty here is the fact that peptide is relatively small, and may be buried by following blocking agent, and therefore it will be impossible to generate standard curve. Briefly, the plate was coated with serial dilutions of 50 ng/ml of phosphopeptide overnight at 4° C., blocked by blocking buffer, washed, and probed with biotinylated primary antibodies.

Figure 5:
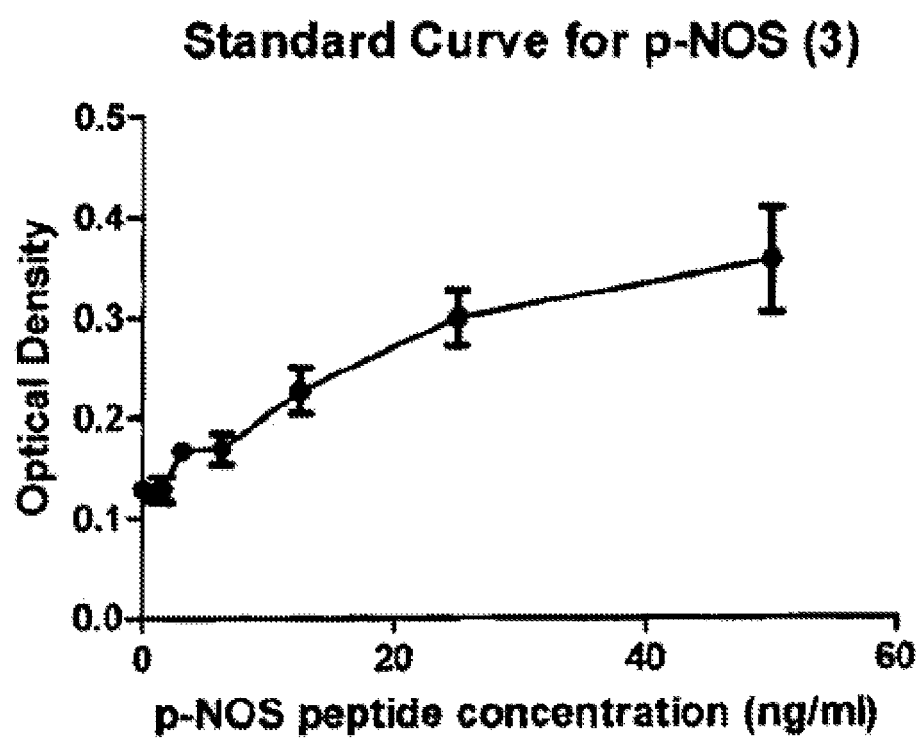
FIG. 5 shows a standard curve for p-NOS.
Figure 6:
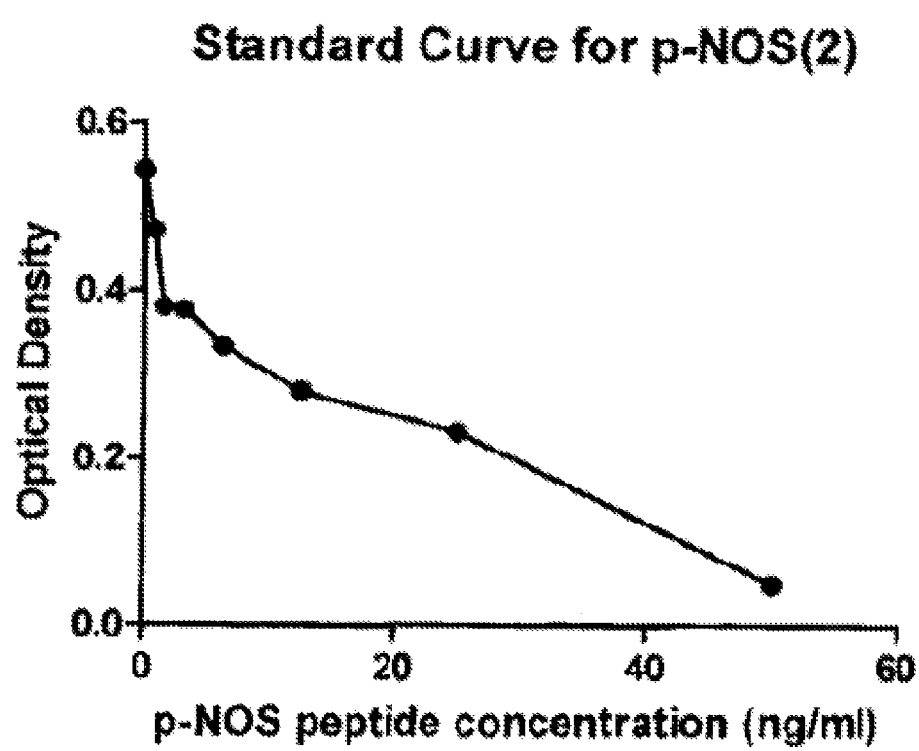
FIG. 6 shows a standard curve for p-NOS using a phosphorylated peptide.
Figure 7:
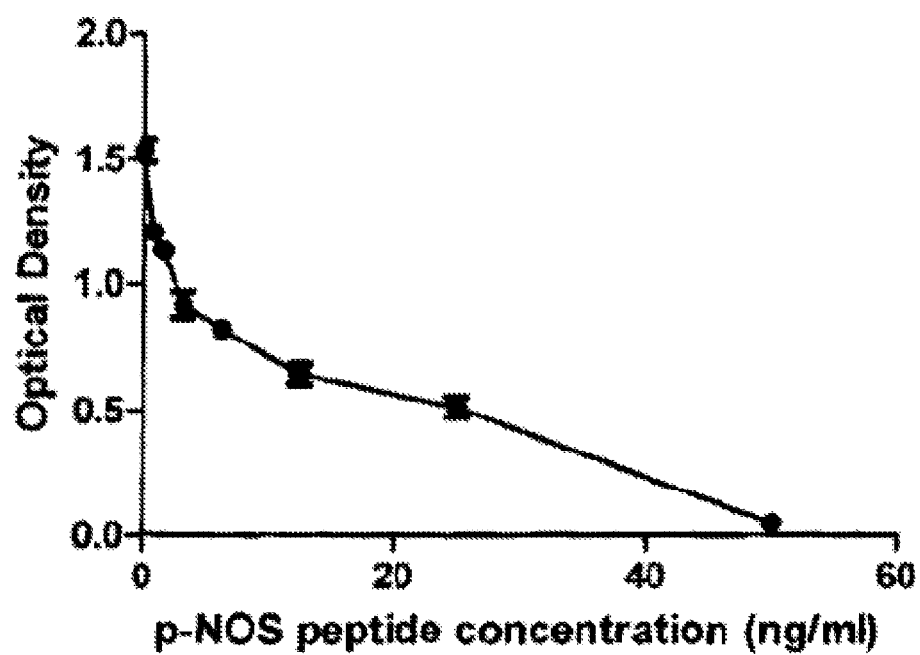
FIG. 7 shows a standard curve for p-NOS using another phosphorylated peptide.
Figure 8:
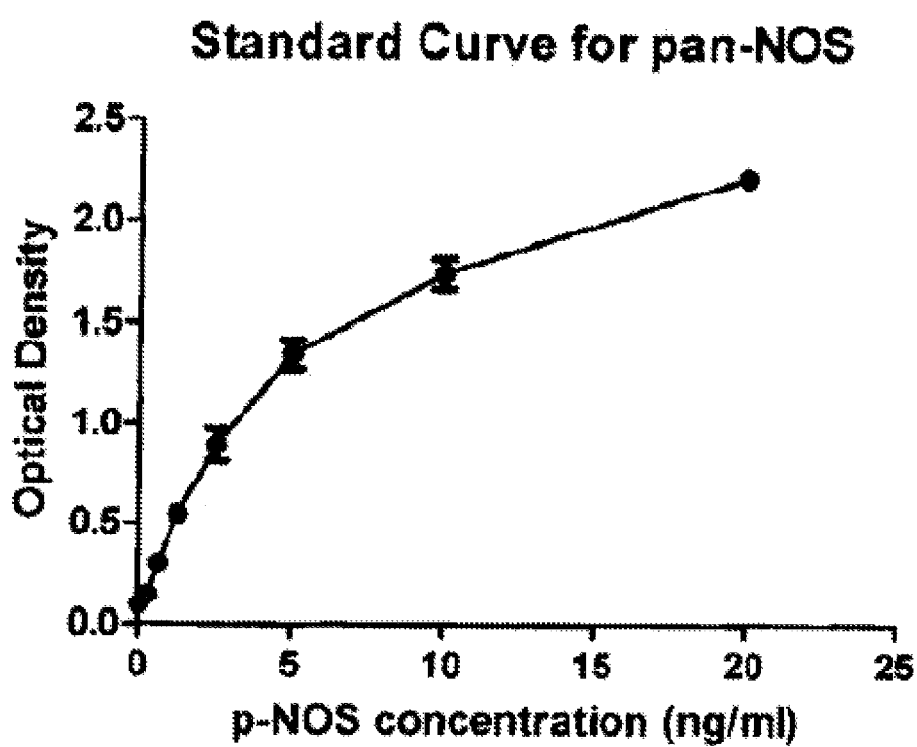
FIG. 8 shows a standard curve for pan-NOS.
Figure 9:
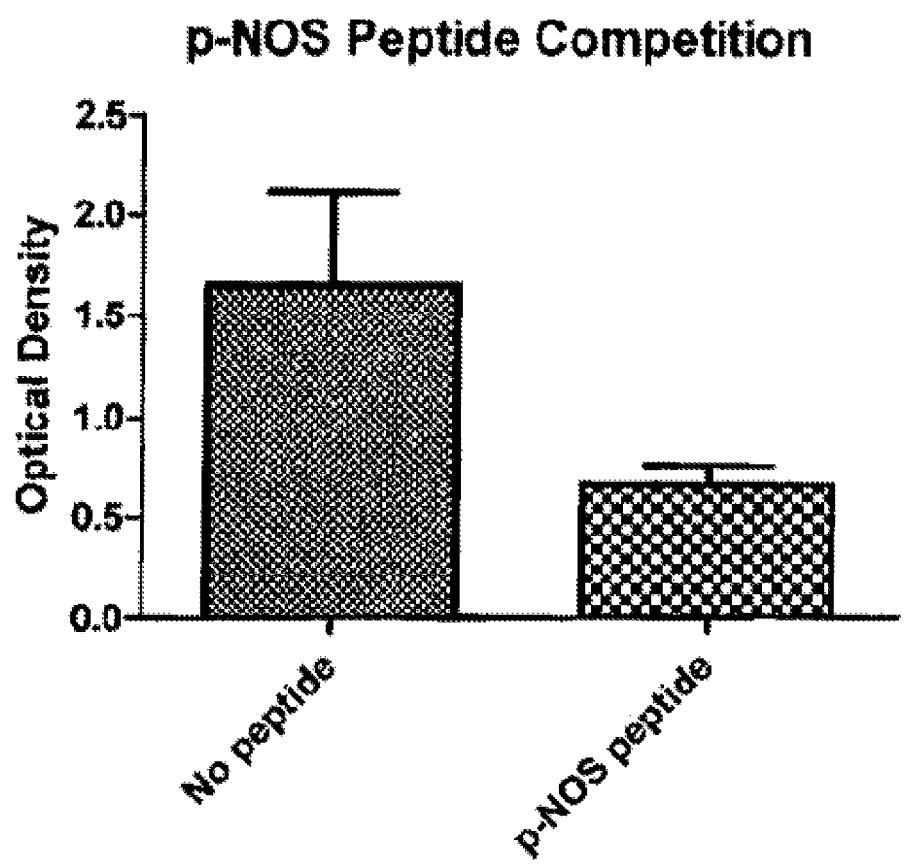
FIG. 9 is a graph showing p-NOS peptide competition.

The results are shown in FIG. 5. Though it may work as standard curve, the range of the y axis is narrow. Better results were obtained using another approach, which mirrors the ones using in ELISAs of small molecules. For that purpose, phosphor-peptide was biotinylated, and coated with phosphor-specific antibodies microplates were incubated with different concentrations of biotinylated phosphor-peptide to generate standard curve. In this case, the wells with samples are allowed to react first, and thereafter the peptide is added, that is why the more absorbance will have the well, the less actual nNOS concentration is in this well. The results of two peptides, obtained from two different companies are shown in FIGS. 6 and 7. As seen, the latter peptide is preferable for standard curve generation and quantification, since the y axis has a bigger range. Standard curve for pan-NOS was generated using commercially available rat nNOS in the format of indirect ELISA. The results are shown in FIG. 8. The peptide used is specific for Ser852 phosphorylation site of human nNOS, as it blocked the signal from samples probed with phospho-specific antibodies to nNOS (see FIG. 9). In conclusion, the results of the developed ELISA for phosphorylated at Ser852 human nNOS shows that this is rapid, convenient and sensitive assay that can be used for quantification of phosphor-nNOS, as well as p-NOS/pan-NOS ratio of this protein in human samples.

ELISA Protocol for Measuring Neuronal pNOS/NOS Ratio at Ser852 in Human Samples

The current protocol is designed to measure pNOS 1/NOS 1 ratio at Ser852 in human/mouse samples, as serum, amniotic fluid or cell lysates, using 96-well microplate. An immobilized capture antibody for pNOS1 or panNOS1 binds either pNOS1 or total NOSI (regardless of phosphorylation status) present in samples. After blocking and sample incubation, the unbound material is washed away, and a biotinylated detection antibody specific for panNOS is used to detect the protein utilizing a standard streptavidin-HRP format. Average for blank readings is subtracted from the averages for the duplicate readings for each sample. The absorbance at 450 run of the phosphorylated protein is normalized to that of the pan-protein in each well.

Materials.

Total NOS 1 capture antibody, Santa Cruz Biotechnology, Catalog#sc55521

Phospho-specific (Ser852) capture antibody for pNOS 1, Santa Cruz Biotechnology, Catalog#sc19826

Detection panNOS1 antibody, Santa Cruz Biotechnology, Catalog#sc55521

Streptavidin-HRP, R&D Systems Catalog#DY998

Substrate reagent (TMB), R&D Systems Catalog#DY999

Stop solution, R&D Systems Catalog#DY994

96 well microplates, R&D Systems, Catalog#DY990

Plate sealers, R&D Systems, Catalog #DY992

Aprotinin, Sigma, Catalog #A6279

Leupeptin, Sigma, Catalog#L8511

Pepstatin, Sigma, Catalog #P4265

Phenylmethylsulfonylfluoride (PMSF), Sigma, Catalog #P7626)

Sodium azide (NaN3), Sigma, Catalog#52002)

EDT A, Sigma, Catalog #E7889-100 ml

Triton X-1 00, Sigma, Catalog#T9284

Tween 20, Sigma, Catalog#P7949-100 ml

Manifold dispenser, pipettes and pipette tips

Deionized or distilled water

PBS—137 rnM NaCl, 2.7 mM KCl, 8.1 mM Na2HP04, 1.5 mM KH2P04, pH 7.2-7.4, 0.2 µrn filtered Wash Buffer—0.05% Tween 20 in PBS, pH 7.2-7.4, or use R&D Systems, Catalog#WA126

Block Buffer—1% BSA (Sigma, Catalog#A9647-1 OOG), 0.05% NaN3, in PBS, pH 7.2-7.4.

Detection antibody diluent—1% BSA in PBS, pH 7.2-7.4

Streptavidin-HRP diluent—I % BSA in PBS, pH 7.2-7.4

Sample diluent—1 mM EDTA, 0.5% Triton X-100 in PBS, pH 7.2-7.4

Lysis Buffer—1 mM EDTA, 0.005% Tween 20, 0.5% Triton X-100, 10 g/mL

Leupeptin, 10 g/mL Pepstatin, 100 M PMSF, 3 g/mL Aprotinin in PBS, pH 7.2-7.4

EZ-link Biotinylation kit, Thermo Scientific, Catalog#21955

Plate Preparation.

1. Dilute the capture antibody to a working concentration of 2.0 g/mL in PBS, without carrier protein Immediately coat a 96 well microplate with 100 μl per well of the diluted capture antibody (panNOS1 or pNOS1 in duplicates). Seal the plate and incubate overnight at 4° C.

2. Aspirate each well and wash with washing buffer, repeating the process two times for a total of 3 washes.

3. Block plates by adding 300 μl of block buffer to each well. Incubate at room temperature for 1-2 hours.

4. Repeat the aspiration/wash as in step 2. The plates are now ready for sample addition.

Assay Procedure.

1. Add 100 μl of sample (or dilute sample 2-4 times) in sample diluent. Cover with a plate sealer and incubate 2 hours at room temperature.

2. Repeat the aspiration/wash as in step 2 of Plate Preparation.

3. Dilute the detection antibody, previously biotinylated according to manufacturer's protocol, to a working concentration of 125 ng/mL in detection antibody diluent (detection panNOS 1 antibody, Santa Cruz Biotechnology, Catalog#sc55521). Add 100 μl of the diluted detection antibody to each well. Cover with a new plate sealer and incubate 2 hours at room temperature.

4. Repeat the aspiration/wash as in step 2 of Plate Preparation.

5. Immediately before use, dilute the streptavidin-HRP to the working concentration specified on the vial label using streptavidin-HRP diluent. Add 100 μl of the diluted streptavidin-HRP to each well. Incubate for 30 minutes at room temperature. Avoid placing the plate in direct light.

6. Repeat the aspiration/wash as in step 2 of the Plate Preparation.

7. Add 100 μl of substrate solution to each well. Incubate for 20 minutes at room temperature. Avoid placing the plate in direct light.

8. Add 50 μl of stop solution to each well. Gently tap the plate to ensure thorough mixing.

9. Determine the optical density of each well immediately, using a microplate reader set to 450 nm. If wavelength correction is available, set to 540 nm or 570 nm. If wavelength correction is not available, subtract readings at 540 nm or 570 nm from the readings at 450 nm.

REFERENCES

1. Calabrese v; Mancuso C, Calvani M. Rizzarelli E, Butterfield A, and A-M Giuffrida S. Nitric oxide in the central nervous system: neuroprotection versus neurotoxicity. Nat Rev Neurosci 8, 766-775, 2007.
2. Brown G C. Nitric oxide and neuronal death. Nitric Oxide, 23, 153-165, 2010.
3. Rameau G A et al. Bidirectional regulation of neuronal nitric-oxide synthase phosphorylation at serine 852 by the N-methyi-D-aspartate receptor. J Bioi Chern, 279, 14307-14, 2004.
4. C-X Luo, D-Y Zhu. Research progress in neurobiology of neuronal nitric oxide synthase. Neurosci. Bull, 27, 23-35, 2011.
5. Hayashi Y, et al. Regulation of neuronal nitric-oxide synthase by calmodulin kinases. J Bioi Chern, 274, 20597-20602, 1999.
6. Komeima K, et al. Inhibition of neuronal nitric-oxide synthase by calcium/calmodulin-dependent protein kinase II through Ser847 phosphorylation in NGJ08-15 neuronal cells. J Bioi Chem, 275, 28139-28143, 2000.

We claim:

1. A method comprising the step of measuring the levels of phosphorylated neuronal nitric oxide synthase (nNOS) (p-NOS) and total nNOS (pan-NOS) by performing an immunoassay with either (a) an amniotic fluid sample obtained from a pregnant female or (b) a cord blood sample obtained from a neonate, wherein the p-NOS is phosphorylated at Ser852 of SEQ ID NO:1.

2. The method of claim 1, wherein the immunoassay is an enzyme-linked immunosorbent assay (ELISA).

* * * * *